(12) United States Patent
Russell et al.

(10) Patent No.: US 12,023,419 B2
(45) Date of Patent: Jul. 2, 2024

(54) PROKARYOTIC COLLAGEN THERAPEUTICS FOR POSTOPERATIVE ADHESIONS

(71) Applicants: The Texas A&M University System, College Station, TX (US); ECM Technologies, LLC, Pearland, TX (US)

(72) Inventors: Brooke Russell, Friendswood, TX (US); Magnus Hook, Houston, TX (US); David McQuillan, Abingdon, MD (US)

(73) Assignees: ECM TECHNOLOGIES, LLC, Houston, TX (US); THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 15/898,482

(22) Filed: Feb. 17, 2018

(65) Prior Publication Data
US 2018/0236141 A1 Aug. 23, 2018

Related U.S. Application Data

(60) Provisional application No. 62/460,284, filed on Feb. 17, 2017.

(51) Int. Cl.
| | | |
|---|---|---|
| *A61L 31/04* | (2006.01) | |
| *A61K 9/06* | (2006.01) | |
| *A61K 9/08* | (2006.01) | |
| *A61K 9/12* | (2006.01) | |
| *A61K 9/19* | (2006.01) | |
| *A61K 9/70* | (2006.01) | |
| *A61L 15/44* | (2006.01) | |
| *A61L 29/08* | (2006.01) | |
| *A61L 29/16* | (2006.01) | |
| *A61L 31/10* | (2006.01) | |
| *A61L 31/16* | (2006.01) | |
| *C07K 14/78* | (2006.01) | |
| *C12N 15/03* | (2006.01) | |
| *C12N 15/62* | (2006.01) | |

(52) U.S. Cl.
CPC ............ *A61L 31/044* (2013.01); *A61K 9/06* (2013.01); *A61K 9/08* (2013.01); *A61K 9/12* (2013.01); *A61K 9/122* (2013.01); *A61K 9/19* (2013.01); *A61K 9/7007* (2013.01); *A61L 15/44* (2013.01); *A61L 29/085* (2013.01); *A61L 29/16* (2013.01); *A61L 31/10* (2013.01); *A61L 31/16* (2013.01); *C07K 14/78* (2013.01); *C12N 15/03* (2013.01); *C12N 15/62* (2013.01); *A61L 2300/252* (2013.01); *A61L 2300/424* (2013.01); *A61L 2420/02* (2013.01); *Y02A 50/30* (2018.01)

(58) Field of Classification Search
CPC ............................ A61L 31/044; C07K 14/78
See application file for complete search history.

(56) References Cited

U.S. PATENT DOCUMENTS

| | | | |
|---|---|---|---|
| 6,391,939 B2 | 5/2002 | Tayot et al. | |
| 6,521,223 B1 | 2/2003 | Calais et al. | |
| 2007/0099244 A1* | 5/2007 | Xu ................ | C07K 14/78 435/7.2 |
| 2009/0203627 A1* | 8/2009 | Hook .............. | C07K 14/78 514/21.5 |
| 2011/0288274 A1* | 11/2011 | Russell .......... | C07K 14/78 530/356 |
| 2012/0208768 A1* | 8/2012 | Hook .............. | C07K 14/78 514/19.2 |
| 2013/0150300 A1* | 6/2013 | Hook .............. | C07K 14/78 514/13.3 |
| 2014/0163205 A1* | 6/2014 | Russell .......... | C07K 14/78 530/356 |
| 2015/0272729 A1* | 10/2015 | Wagner .......... | A61F 2/82 623/1.15 |
| 2016/0235832 A1 | 8/2016 | Ko et al. | |
| 2016/0376326 A1 | 12/2016 | Ramshaw et al. | |
| 2017/0044220 A1 | 2/2017 | Mirochnitchenko et al. | |

FOREIGN PATENT DOCUMENTS

WO    2018152444 A1    8/2018

OTHER PUBLICATIONS

Peng et al., 2013, Engineering multiple biological functional motifs into a blank collagen-like protein template from *Streptococcus pyogenes*, Journal of Biomedical Materials Research, 102A(7):2189-2196.*
Stahl et al., 2012, Encoding Cell-Instructive Cues to PEG-Based Hydrogels via Triple Helical Peptide Assembly, Soft Matter, 8: 10409-10418.*
Luo et al., 2011, Self-Assembly of Collagen-Mimetic Peptide Amphiphiles into Biofunctional Nanofiber, ACSNANO, 5(10): 7739-7747.*
Yao et al., 2004, Design, Expression and Characterization of Collagen-Like Proteins Based on the Cell Adhesive and Crosslinking Sequences Derived from Native Collagens, J Biochem, 136: 643-649.*
Cosgriff-Hernandez et al., 2010, Bioactive hydrogels based on Designer Collagens, Acta Biomaterialia, 6: 3969-3977.*
Haust et al., 1960, The Role of Smooth Muscle Cells in the Fibrogenesis of Arteriosclerosis, The American Journal of Pathology, XXXVII(4): 377-389.*

(Continued)

*Primary Examiner* — Amber D Steele
(74) *Attorney, Agent, or Firm* — Edwin S. Flores; Chalker Flores, LLP

(57) ABSTRACT

The present invention includes a synthetic collagen that facilitates adhesion prevention and methods of use thereof. The present invention includes a prokaryotic collagen that facilitates adhesion prevention and treatment and methods of use thereof. The prokaryotic collagen includes an isolated and purified triple helical backbone protein that facilitates adhesion prevention: one or more alteration in a triple helical backbone protein sequence, and one or more binding motifs, wherein the isolated and purified triple helical backbone protein facilitates adhesion prevention.

6 Claims, 5 Drawing Sheets
Specification includes a Sequence Listing.

(56) References Cited

OTHER PUBLICATIONS

Mahdy, 2019, Skeletal muscle fibrosis: an overview, Cell and Tissue Research, 375: 575-588.*

Bachmann et al., 2022, Fibrotic Signaling in Cardiac Fibroblasts and Vascular Smooth Muscle Cells: The Dual Roles of Fibrosis in HFpEF and CAD, Cells, 11: 1657 (33 pages).*

Jalan, et al. "Simultaneous Control of Composition and Register of an AAB-Type Collagen Heterotrimer" ACS Publications, American Chemical Society, Published Dec. 4, 2012, 7 pp.

United States Patent and Trademark Office (ISA), International Search Report and Written Opinion for PCT/US2018/018549 dated Jul. 5, 2018, 14 pp.

* cited by examiner

FIG. 1A     DC1:

MNHKVHHHHHHMELDEQEEKAKVRTELIQELAQGLGGIEKKNFPTLGDEDLDHTYMTKLLTYLQEREQ
AENSWRKRLLKGIQDHALDGQDGRNGERGEQGPTGPTGPAGPRGLQGLQGLQGERGEQGPTGPAGPRG
LQGERGEQGPTGLAGKAGEAGAKGETGPAGPQGPRGEQGPQGLPGKDGEAGAQGPAGPMGPAGERGEK
GEPGTQGAKGDRGETGPVGPRGERGEAGPAGKDGERGPVGPAGKDGQNGQDGLPGKDGKDGQNGKDGL
PGKDGKDGQNGKDGLPGKDGKDGQDGKDGLPGKDGKDGLPGKDGKDGQPGKPAPKTPEVPQKPDTAP
(SEQ ID NO:1)

FIG. 1B     DC1collagendomain:

GQDGRNGERGEQGPTGPTGPAGPRGLQGLQGLQGERGEQGPTGPAGPRGLQGERGEQGPTGLAGKAGE
AGAKGETGPAGPQGPRGEQGPQGLPGKDGEAGAQGPAGPMGPAGERGEKGEPGTQGAKGDRGETGPVG
PRGERGEAGPAGKDGERGPVGPAGKDGQNGQDGLPGKDGKDGQNGKDGLPGKDGKDGQNGKDGLPGKD
GKDGQDGKDGLPGKDGKDGLPGKDGKDGQPGKP     (SEQ ID NO:2)

FIG. 1C     DC2:

MNHKVHHHHHHMELDEQEEKAKVRTELIQELAQGLGGIEKKNFPTLGDEDLDHTYMTKLLTYLQEREQ
AENSWRKRLLKGIQDHALDGQDGRNGERGEQGPTGPTGPAGPRGLQGLQGFPGERGEQGPTGPAGPRG
LQGERGEQGPTGLAGKAGEAGAKGETGPAGPQGPRGEQGPQGLPGKDGEAGAQGPAGPMGPAGERGEK
GEPGTQGAKGDRGETGPVGPRGERGEAGPAGKDGERGPVGPAGKDGQNGQDGLPGKDGKDGQNGKDGL
PGKDGKDGQNGKDGLPGKDGKDGQDGKDGLPGKDGKDGLPGKDGKDGQPGKPAPKTPEVPQKPDTAP
(SEQ ID NO:3)

FIG. 1D     DC2 collagendomain:

GQDGRNGERGEQGPTGPTGPAGPRGLQGLQGFPGERGEQGPTGPAGPRGLQGERGEQGPTGLAGKAGE
AGAKGETGPAGPQGPRGEQGPQGLPGKDGEAGAQGPAGPMGPAGERGEKGEPGTQGAKGDRGETGPVG
PRGERGEAGPAGKDGERGPVGPAGKDGQNGQDGLPGKDGKDGQNGKDGLPGKDGKDGQNGKDGLPGKD
GKDGQDGKDGLPGKDGKDGLPGKDGKDGQPGKP     (SEQ ID NO:4)

FIG. 1E     ecollagen:

MNHKVHHHHHHMELDEQEEKAKVRTELIQELAQGLGGIEKKNFPTLGDEDLDHTYMTKLLTYLQEREQ
AENSWRKRLLKGIQDHALDGQDGRNGERGEQGPTGPTGPAGPRGLQGLQGFPGERGEQGPTGPAGPRG
LQGERGEQGPTGLAGKAGEAGAKGETGPAGPQGPRGEQGPQGLPGRDGEAGAQGPAGPMGPAGERGEK
GEPGTQGAKGDRGETGPVGPRGERGEAGPAGRDGERGPVGPAGRDGQNGQDGLPGKDGRDGQNGRDGL
PGRDGRDGQNGRDGLPGRDGRDGQDGRDGLPGRDGRDGLPGdrGerGQPGRPAPKTPEVPQKPDTAP
(SEQ ID NO:5)

FIG. 1F     ecollagencollagendomain:

GQDGRNGERGEQGPTGPTGPAGPRGLQGLQGFPGERGEQGPTGPAGPRGLQGERGEQGPTGLAGKAGE
AGAKGETGPAGPQGPRGEQGPQGLPGRDGEAGAQGPAGPMGPAGERGEKGEPGTQGAKGDRGETGPVG
PRGERGEAGPAGRDGERGPVGPAGRDGQNGQDGLPGKDGRDGQNGRDGLPGRDGRDGQNGRDGLPGRD
GRDGQDGRDGLPGRDGRDGLPGDRGERGQPGRP     (SEQ ID NO:6)

FIG. 1G  DC2-3x:

MNHKVHHHHHHMELDEQEEKAKVRTELIQELAQGLGGIEKKNFPTLGDEDLDHTYMTKLLTYLQEREQ
AENSWRKRLLKGIQDHALDGQDGRNGERGEQGPTGPTGPAGPRGLQGLQGFPGERGEQGPTGPAGPRG
LQGERGEQGPTGLAGKAGEAGAKGETGPAGPQGPRGEQGPQGLPGFPGERGAQGPAGPMGPAGERGEK
GEPGTQGAKGDRGETGPVGPRGERGEAGPAGKDGERGPVGPAGKDGQNGQDGFPGKDGKDGQNGKDGL
PGKDGKDGQNGKDGLPGKDGKDGQDGKDGLPGKDGKDGFPGERGKDGQPGKPAPKTPEVPQKPDTAP
(SEQ ID NO:7)

FIG. 1H  DC2-3xcollagendomain:

GQDGRNGERGEQGPTGPTGPAGPRGLQGLQGFPGERGEQGPTGPAGPRGLQGERGEQGPTGLAGKAGE
AGAKGETGPAGPQGPRGEQGPQGLPGFPGERGAQGPAGPMGPAGERGEKGEPGTQGAKGDRGETGPVG
PRGERGEAGPAGKDGERGPVGPAGKDGQNGQDGFPGKDGKDGQNGKDGLPGKDGKDGQNGKDGLPGKD
GKDGQDGKDGLPGKDGKDGFPGERGKDGQPGKP  (SEQ ID NO:8)

FIG. 1I  DC2-FN:

MNHKVHHHHHHMELDEQEEKAKVRTELIQELAQGLGGIEKKNFPTLGDEDLDHTYMTKLLTYLQEREQ
AENSWRKRLLKGIQDHALDGQDGRNGERGEQGPTGPTGPAGPRGLQGLQGFPGERGEQGPTGPAGPRG
LQGERGEQGPTGLAGKAGEAGAKGETGPAGPQGPRGEQGPQGLPGKDGEAGAQGPAGPMGPAGERGEK
GEPGTQGAKGDRGETGPVGPRGERGEAGPAGKDGERGPVGPAGKDGQNGQDGLPGKDGKDGQNGKDGL
PGKDGKDGQNGKDGLPGKDGKDGQDGKDGLPGKDGKDGLPGKDGLAGQRGIVGLPGQRGERAPKTPEV
PQKPDTAP  (SEQ ID NO:9)

FIG. 1J  DC2-FNcollagendomain:

GQDGRNGERGEQGPTGPTGPAGPRGLQGLQGFPGERGEQGPTGPAGPRGLQGERGEQGPTGLAGKAGE
AGAKGETGPAGPQGPRGEQGPQGLPGKDGEAGAQGPAGPMGPAGERGEKGEPGTQGAKGDRGETGPVG
PRGERGEAGPAGKDGERGPVGPAGKDGQNGQDGLPGKDGKDGQNGKDGLPGKDGKDGQNGKDGLPGKD
GKDGQDGKDGLPGKDGKDGLPGKDGLAGQRGIVGLPGQRGER  (SEQ ID NO:10)

FIG. 1K  DC2-Thrombin:

MNHKVHHHHHHMELDEQEEKAKVRTELIQELAQGLGGIEKKNFPTLGDEDLDHTYMTKLLTYLQEREQ
AENSWRKRLLKGIQDHALDLVPRGSPGLPGPRGQDGRNGERGEQGPTGPTGPAGPRGLQGLQGFPGER
GEQGPTGPAGPRGLQGERGEQGPTGLAGKAGEAGAKGETGPAGPQGPRGEQGPQGLPGKDGEAGAQGP
AGPMGPAGERGEKGEPGTQGAKGDRGETGPVGPRGERGEAGPAGKDGERGPVGPAGKDGQNGQDGLPG
KDGKDGQNGKDGLPGKDGKDGQNGKDGLPGKDGKDGQDGKDGLPGKDGKDGLPGKDGKDGQPGKPAPK
TPEVPQKPDTAP  (SEQ ID NO:11)

FIG. 1L  DC2-Thrombincollagendomain:

GSPGLPGPRGQDGRNGERGEQGPTGPTGPAGPRGLQGLQGFPGERGEQGPTGPAGPRGLQGERGEQGP
TGLAGKAGEAGAKGETGPAGPQGPRGEQGPQGLPGKDGEAGAQGPAGPMGPAGERGEKGEPGTQGAKG
DRGETGPVGPRGERGEAGPAGKDGERGPVGPAGKDGQNGQDGLPGKDGKDGQNGKDGLPGKDGKDGQN
GKDGLPGKDGKDGQDGKDGLPGKDGKDGLPGKDGKDGQPGKP  (SEQ ID NO:12)

FIG. 1M    DC2-Pepsin:

MNHKVHHHHHHMELDEQEEKAKVRTELIQELAQGLGGIEKKNFPTLGDEDLDHTYMTKLLTYLQEREQ
AENSWRKRLLKGIQDHALDNLYVGLPGPRGQDGRNGERGEQGPTGPTGPAGPRGLQGLQGFPGERGEQ
GPTGPAGPRGLQGERGEQGPTGLAGKAGEAGAKGETGPAGPQGPRGEQGPQGLPGKDGEAGAQGPAGP
MGPAGERGEKGEPGTQGAKGDRGETGPVGPRGERGEAGPAGKDGERGPVGPAGKDGQNGQDGLPGKDG
KDGQNGKDGLPGKDGKDGQNGKDGLPGKDGKDGQDGKDGLPGKDGKDGLPGKDGKDGQPGKPAPKTPE
VPQKPDTAP    (SEQ ID NO:13)

FIG. 1N    DC2-Pepsincollagendomain:

GLPGPRGQDGRNGERGEQGPTGPTGPAGPRGLQGLQGFPGERGEQGPTGPAGPRGLQGERGEQGPTGL
AGKAGEAGAKGETGPAGPQGPRGEQGPQGLPGKDGEAGAQGPAGPMGPAGERGEKGEPGTQGAKGDRG
ETGPVGPRGERGEAGPAGKDGERGPVGPAGKDGQNGQDGLPGKDGKDGQNGKDGLPGKDGKDGQNGKD
GLPGKDGKDGQDGKDGLPGKDGKDGLPGKDGKDGQPGKP    (SEQ ID NO:14)

FIG. 1O    DC1-DDR1:

MNHKVHHHHHHMELDEQEEKAKVRTELIQELAQGLGGIEKKNFPTLGDEDLDHTYMTKLLTYLQEREQ
AENSWRKRLLKGIQDHALDGQDGRNGERGEQGPTGPTGPAGPRGLQGLQGLQGERGEQGPTGPAGPRG
LQGERGEQGPTGLAGKAGEAGAKGETGPAGPQGPRGEQGVMGFPGKDGEAGAQGPAGPMGPAGERGEK
GEPGTQGAKGDRGETGPVGPRGERGEAGPAGKDGERGPVGPAGKDGQNGQDGLPGKDGKDGQNGKDGL
PGKDGKDGQNGKDGLPGKDGKDGQDGKDGLPGKDGKDGLPGKDGKDGQPGKPAPKTPEVPQKPDTAP
(SEQ ID NO:15)

FIG. 1P    DC1-DDR1collagendomain:

GQDGRNGERGEQGPTGPTGPAGPRGLQGLQGLQGERGEQGPTGPAGPRGLQGERGEQGPTGLAGKAGE
AGAKGETGPAGPQGPRGEQGVMGFPGKDGEAGAQGPAGPMGPAGERGEKGEPGTQGAKGDRGETGPVG
PRGERGEAGPAGKDGERGPVGPAGKDGQNGQDGLPGKDGKDGQNGKDGLPGKDGKDGQNGKDGLPGKD
GKDGQDGKDGLPGKDGKDGLPGKDGKDGQPGKP    (SEQ ID NO:16)

★ = peritoneal wall resection

● = cecal serosal abrasion

▲ = Suture holding cecum in proximity to body wall defect

PROKARYOTIC COLLAGEN THERAPEUTICS FOR POSTOPERATIVE ADHESIONS

CROSS-REFERENCE TO RELATED APPLICATIONS

This Patent Application claims priority to U.S. Provisional Patent Application No. 62/460,284, filed Feb. 17, 2017, the entire contents of which is incorporated herein by reference.

TECHNICAL FIELD OF THE INVENTION

The present invention relates generally to methods and compositions used in connection with reducing postoperative adhesion formations.

STATEMENT OF FEDERALLY FUNDED RESEARCH

None.

REFERENCE TO A SEQUENCE LISTING

The present application includes a Sequence Listing filed separately as required by 37 CFR 1.821-1.825.

BACKGROUND OF THE INVENTION

Adhesion formation is a complication of many types of surgical procedures, and particularly abdominal and bowel surgeries. Adhesion formation typically occurs as a result of the formation of a fibrin clot, which transforms into scar tissue connecting different tissues that are normally separated. It is often necessary to surgically remove the adhesion; however reoccurrence often occurs.

Current adhesion prevention techniques revolve around interrupting the adhesion formation mechanism, which is believed to result from the diffusion of fibrinogen into the space between the tissues subject to surgical trauma, thereby causing the formation of fibrin clots. Inflammation is also thought to play a role in adhesion formation.

For example, U.S. Pat. No. 6,521,223, entitled, "Single phase gels for the prevention of adhesions," disclosed a single-phase gel for preventing the formation of surgical adhesions are disclosed. The gels are prepared by reacting an aqueous solution of a polyanionic polysaccharide, such as hyaluronic acid or carboxymethyl cellulose, with divinyl sulfone, to form a gel, the solution is neutralized, and a solid is precipitated from the solution.

Yet another example is U.S. Pat. No. 6,391,939, entitled, "Collagenic material useful in particular for preventing post-operative adhesions", and is said to teach a biocompatible collagenous material which is non-toxic and biodegradable in less than one month, and preferably in less than one week. The material includes collagen and at least one hydrophilic macromolecular additive that are chemically non-reactive towards the collagen, with the collagen having at least partially lost its helical structure and being cross-linked. The collagenous material is said to be used for preventing post-operative adhesions.

However, a need remains for compositions and method that prevent adhesions, e.g., post-operative adhesions that is biocompatible and that does not trigger an immune response.

SUMMARY OF THE INVENTION

The present invention provides recombinant collagen-like protein that has demonstrated efficacy with regard to postoperative adhesion formation.

In one embodiment, the present invention includes a non-thrombogenic collagen fusion protein that reduces or eliminates postoperative adhesions, the fusion comprising: a triple helical non-thrombogenic backbone protein; and one or more triple helix forming peptide motifs in the triple helical non-thrombogenic backbone protein, wherein the fusion protein reduces or eliminates postoperative adhesions. In one aspect, the fusion protein further comprises one or more biocompatible carriers adapted for application inside a body cavity. In another aspect, the triple helix forming peptides are selected from SEQ ID NOS: 1 to 16. In another aspect, the fusion protein is produced in a prokaryotic expression system. In another aspect, the triple helical backbone is derived from a *Streptococcus, Bacillus, Legionella, Clostridium, Solibacter, Rhodopseudomonas, Methylobacteriumor*, a viral collagen protein. In another aspect, the fusion protein further comprises one or more binding motifs comprises an integrins binding site, a matrix metalloproteinase (MMP) binding site, a discoidin domain-containing receptor (DDR) binding site, a fibronectin binding site, a bone sialoprotein binding site, a heparin binding site, a decorin binding site, a fibromodulin binding site, a lumican binding sites, or other binding sites. In another aspect, the triple helix forming peptide motifs are selected from DC1, DC2, DC3, DC2-3x, DC2-FN, and Type 1 Collagen. In another aspect, the fusion protein has 85, 86, 87, 88, 89, 90, 91, 92, 93, 94, 95, 95, 97 98, or 99% homology to the sequence DC1, DC2, DC3, DC2-3x, DC2-FN, Type 1 Collagen, and PBS. In another aspect, the triple helix forming peptide motifs are selected from at least one of DC2-3X, DC2-FN, or CT-1. In another aspect, the triple helix forming peptide motifs are human. In another aspect, the fusion protein interacts with $\alpha1$, $\beta1$, $\alpha2$ integrins or a combination thereof. In another aspect, the fusion protein has a higher melting temperature than an unmodified triple helical backbone protein.

In another embodiment, the present invention includes a method of reducing or eliminating tissue adhesion or fibrosis comprising the steps of: providing a non-thrombogenic collagen fusion protein that facilitates reducing adhesions, wherein the fusion protein comprises: a non-thrombogenic bacterial or viral collagen backbone interspersed with one or more triple helix forming peptide motifs that show a reduced adhesion, wherein the fusion protein reduces or eliminates postoperative adhesions, in a biocompatible carrier; and applying the non-thrombogenic collagen to the damaged area to reduce an adhesion. In one aspect, a damaged area in need of preventing adhesion is an incision. In another aspect, the biocompatible carrier comprises a spray, a foam, a gel, a sheet, a strip, a tube, liquid, a paste, a wax or other material. In another aspect, the biocompatible carrier comprises one or more polymers or other extracellular matrix (ECM) materials to achieve appropriate tensile strength or architecture desired. In another aspect, the non-thrombogenic collagen backbone is selected from a bacterial source with examples *Streptococcus, Bacillus, Legionella, Clostridium, Solibacter, Rhodopseudomonas, Methylobacteriumor*, or a viral collagen. In another aspect, a site for tissue adhesion is an open surgery, minimally invasive surgery, hernia, open-heart surgery, surgery of a ligament, meniscus, patella, mouth sores and oral lesions, tissue bone regeneration, periodontal regeneration, oral reconstruction, vestibuloplasty, tissue regeneration around dental implants, esophagus reconstruction, plastic surgery, cosmetic surgery, peripheral arterial disease, ladder reconstruction, orbital floor repair, treatment of ulcers, corneal repair, adhesion in spinal implant procedures, adhesion in general surgery, vascular conduits, gingival, genitourinary reconstruction, celioscopy, nasoscopy, laryngoscopy, endoscopy, procedure for peritoneal dialysis or laparoscopy. In another aspect, the fibrosis is from a fibrosing disease, scleroderma, pulmonary fibrosis, asthma, keloid scarring, rheumatoid arthritis, lupus, nephrogenic fibrosing dermopathy, fibrotic lesions formed after *Schistosoma japonicum* infection, autoimmune diseases, Lyme disease, stromal remodeling in pancreatitis and stromal fibrosis, chronic obstructive pulmonary disease, uterine fibroids, ovarian fibrosis, other fibrocystic formations, corneal fibrosis or other eye fibrosis, such as that resulting from corneal refraction surgery, fibrosis resulting from congestive heart failure and other post-ischemic conditions, abdominal adhesions, wide angle glaucoma trabeculotomy, endometriosis, and any combinations thereof.

In another embodiment, the present invention includes a kit comprising: a non-thrombogenic fusion protein comprising: an isolated and purified triple helical bacterial backbone protein that reduces or eliminates postoperative adhesions and one or more triple helix forming peptide motifs, wherein the fusion protein reduces or eliminates postoperative adhesions; and instructions for use of the same. In one aspect, the fusion protein is lyophilized. In another aspect, the fusion protein is adapted for irrigation of a surgical site to prevent or reduce adhesion of a surgical site selected from: open surgery, minimally invasive surgery, hernia, open-heart surgery, surgery of a ligament, meniscus, patella, mouth sores and oral lesions, tissue bone regeneration, periodontal regeneration, oral reconstruction, vestibuloplasty, tissue regeneration around dental implants, esophagus reconstruction, plastic surgery, cosmetic surgery, peripheral arterial disease, ladder reconstruction, orbital floor repair, treatment of ulcers, corneal repair, adhesion in spinal implant procedures, adhesion in general surgery, vascular conduits, gingival, genitourinary reconstruction, celioscopy, nasoscopy, laryngoscopy, endoscopy, or laparoscopy. In another aspect, the kit further comprises at least one of: a polymeric matrix that comprises a biodegradable polymer, a non-biodegradable polymer, a mixture of biodegradable and non-biodegradable polymers, or a copolymer comprising biodegradable and non-biodegradable units, or a physiological buffer. In another aspect, the biodegradable polymer is selected from the group consisting of poly(lactide), poly(glycolide), poly(lactide-co-glycolide), poly(lactic acid), poly(glycolic acid), poly(lactic acid-co-glycolic acid), polyanhydride, polyorthoester, polyetherester, polycaprolactone, polyesteramide, block copolymers of polyethylene glycol and lactide or glycolide, and blends and copolymers thereof. In another aspect, the non-biodegradable polymer is selected from the group consisting of non-biodegradable polyacrylate, polymers of ethylene-vinyl acetate, polymers of acyl-substituted cellulose acetate, non-degradable polyurethane, polystyrene, polyvinyl chloride, polyvinyl fluoride, poly(vinyl imidazole), chlorosulphonate polyolefin, polyethylene oxide, and blends and copolymers thereof. In another aspect, the kit further comprises a biologically active agent selected from at least one of: amoxicillin, ampicillin, azlocillin, aztreonam, azithromycin, bacitracin, bifonazole, butoconazole, butenafine, colistin, carbomer, cyclosporin, carmellose, carbenicillin, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, chloramphenicol, ciprofloxacin, cilastatin, clindamycin, clarithromycin, cloxacillin, clotrimazole, dicloxacillin, doxycycline, dirithromycin, dextran, demeclocycline, ertapenem, ethambutol, erythromycin, fenticonazole, fosfomycin, fusidic acid, furazolidone, flucytosine, fluconazole, gatifloxacin, griseofulvin, gentamicin, gentian violet, haloprogin, herimycin, hyaluronic acid, itraconazole, kanamycin, neomycin, netilmicin, streptomycin, tobramycin, paromomycin, loracarbef, lincoamycin, isoniazid, linezolid, metronidazole, meropenem, teicoplanin, vancomycin, roxithromycin, troleandomycin, telithromycin, spectinomycin, flucloxacillin, mezlocillin, minocycline, nafcillin, oxytetracycline, oxiconazole, penicillin, peperacillin, polymyxin B, enoxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, tetracycline, mupirocin, nitrofurantoin, platensimycin, pyrazinamide, quinupristin/dalfopristin, rifampin/rifampicin, tinidazole, ticarcillin, miconazole, ketoconazole, econazole, isoconazole, sertaconazole, sulconazole, tioconazole, ravuconazole, posaconazole, voriconazole, teronazole, terbinafine, tolnaftate, or undecylenic acid. In another aspect, the physiological buffer comprises physiological saline. In another aspect, the kit further comprises a biocompatible carrier comprises a spray, a foam, a gel, a sheet, a strip, a tube, liquid, a paste, a wax or other material.

In another embodiment, the present invention includes a biocompatible formulation comprising a non-thrombogenic collagen comprising an isolated and purified triple helical protein, wherein the protein reduces or eliminates postoperative adhesions, and one or more biocompatible agents. In another aspect, the biocompatible agents are selected from biologically active agent selected from at least one of: amoxicillin, ampicillin, azlocillin, aztreonam, azithromycin, bacitracin, bifonazole, butoconazole, butenafine, colistin, carbomer, cyclosporin, carmellose, carbenicillin, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, chloramphenicol, ciprofloxacin, cilastatin, clindamycin, clarithromycin, cloxacillin, clotrimazole, dicloxacillin, doxycycline, dirithromycin, dextran, demeclocycline, ertapenem, ethambutol, erythromycin, fenticonazole, fosfomycin, fusidic acid, furazolidone, flucytosine, fluconazole, gatifloxacin, griseofulvin, gentamicin, gentian violet, haloprogin, herimycin, hyaluronic acid, itraconazole, kanamycin, neomycin, netilmicin, streptomycin, tobramycin, paromomycin, loracarbef, lincoamycin, isoniazid, linezolid, metronidazole, meropenem, teicoplanin, vancomycin, roxithromycin, troleandomycin, telithromycin, spectinomycin, flucloxacillin, mezlocillin, minocycline, nafcillin, oxytetracycline, oxiconazole, penicillin, peperacillin, polymyxin B, enoxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, tetracycline, mupirocin, nitrofurantoin, platensimycin, pyrazinamide, quinupristin/dalfopristin, rifampin/rifampicin, tinidazole, ticarcillin, miconazole, ketoconazole, econazole, isoconazole, sertaconazole, sulconazole, tioconazole, ravuconazole, posaconazole, voriconazole, teronazole, terbinafine, tolnaftate, or undecylenic acid. Other non-limiting examples of active agents for use with the fusion protein of the present invention include: a steroidal anti-inflammatory agent, analgesic, sedative, tranquilizer, steroid, antispasmodic, antihistamine, antihypertensive agent, antiviral, oligonucleotide(s), carbohydrate(s), anti-ageing agents, anti-oxidants, vitamins, minerals, preservatives, and any combination thereof.

In another embodiment, the present invention includes a coating applied to a surface of a medical device, the coating comprising: a non-thrombogenic protein comprising an isolated and purified triple helical bacterial protein that reduces or eliminates postoperative adhesions. In one aspect, the medical device is selected from the group consisting of needles, guide wires, meshes, catheters, surgical instruments, equipment for endoscopy, wires, stents, angioplasty balloons, wound drains, wound dressings, arteriovenous shunts, gastroenteric tubes, urethral inserts, laparoscopic equipment, pellets, and implants.

In another embodiment, the present invention includes a method for coating a medical device having a surface comprising: applying to the surface a coating liquid comprising a stabilizing polymer selected from the group consisting of polymers based on cross-linkable acrylic and methacrylic polymers, ethylene acrylic acid copolymers, styrene acrylic copolymers, polyvinyl acetals, ethylene vinyl acetate copolymer, polyvinyl acetate, epoxy resins, amino resins, phenolic resins, copolymers thereof, and combinations; applying a coating liquid comprising a non-thrombogenic collagen, wherein the protein reduces or eliminates postoperative adhesions; and drying to remove liquids such that the crosslinkable acrylic and methacrylic polymers become crosslinked, the fusion protein is entrapped by the stabilizing polymer and the coating adheres to the surface when dry and wet, and remains coherent despite flexing of the surface. In one aspect, the medical device is selected from the group consisting of needles, guide wires, catheters, surgical instruments, equipment for endoscopy, wires, stents, angioplasty balloons, wound drains, wound dressings, arteriovenous shunts, gastroenteric tubes, urethral inserts, laparoscopic equipment, pellets, and implants.

In another embodiment, the present invention includes a method of making a non-thrombogenic fusion protein comprising: providing a triple helical non-thrombogenic collagen backbone protein; and inserting one or more peptide motifs in the triple helical non-thrombogenic collagen backbone protein, wherein the fusion protein reduces or eliminates postoperative adhesions. In one aspect, the one or more peptide motifs are interspersed in the triple helical non-thrombogenic collagen backbone protein to at least one of: increase fusion protein stability or increase a melting point of the fusion protein, when compared to the triple helical non-thrombogenic collagen backbone protein. In another aspect, the fusion protein is selected from SEQ ID NOS: 1 to 16. In another aspect, the fusion protein is produced in a prokaryotic expression system. In another aspect, the triple helical non-thrombogenic collagen backbone protein is selected from at least one of: *Streptococcus, Bacillus, Legionella, Clostridium, Solibacter, Rhodopseudomonas, Methylobacterium*. or a viral collagen protein. In another aspect, the method further comprises adding one or more binding motifs comprises an integrins binding site, a matrix metalloproteinase (MMP) binding site, a discoidin domain-containing receptor (DDR) binding site, a fibronectin binding site, a heparin binding site, a bone sialoprotein binding site, a decorin binding site, a fibromodulin binding site, a lumican binding sites, or other binding sites to the fusion protein.

In another embodiment, the present invention includes an isolated and purified non-thrombogenic collagen provided in an amount sufficient to reduce or eliminate postoperative adhesions.

In another embodiment, the present invention includes a prokaryotic collagen that facilitates wound closure and methods of use thereof. The prokaryotic collagen includes an isolated and purified triple helical backbone protein that facilitates wound closure comprising: one or more alteration in a triple helical backbone protein sequence, and one or more binding motifs, wherein the isolated and purified triple helical backbone protein facilitates wound closure.

In another embodiment, the present invention includes a prokaryotic collagen that facilitates reducing postoperative adhesions comprising: an isolated and purified triple helical backbone protein that facilitates reducing postoperative adhesions comprising: one or more motifs that show a reduced adhesion, wherein the isolated and purified triple helical backbone protein facilitates reducing postoperative adhesions.

In another embodiment, the present invention includes a method of reducing adhesions comprising the steps of: providing a prokaryotic collagen composition that facilitates reducing adhesions, wherein the prokaryotic collagen composition comprises: a biocompatible carrier carrying an isolated and purified triple helical backbone protein that facilitates reducing postoperative adhesions comprising: one or more motifs that show a reduced adhesion, wherein the isolated and purified triple helical backbone protein facilitates reducing postoperative adhesions; and applying the prokaryotic collagen composition to the damaged area to reduce an adhesion.

In another embodiment, the present invention includes composition for use on animals reduce postoperative adhesions. The composition comprises a biocompatible carrier carrying a prokaryotic collagen comprising: an isolated and purified triple helical backbone protein that facilitates reducing postoperative adhesions comprising: one or more motifs that show a reduced adhesion, wherein the isolated and purified triple helical backbone protein facilitates reducing postoperative adhesions. The biocompatible carrier may be a spray, a gel, a sheet, a strip, a tube, liquid, a paste, a wax or other material. The biocompatible carrier may include one or more polymers, or other ECM materials to achieve appropriate tensile strength or architecture desired.

BRIEF DESCRIPTION OF THE DRAWINGS

For a more complete understanding of the features and advantages of the present invention, reference is now made to the detailed description of the invention along with the accompanying figures and in which:

FIGS. 1A-1P are sequence listings. FIG. 1A shows the DC1 sequence (SEQ ID NO:1). FIG. 1B shows the DC1 collagen domain sequence (SEQ ID NO:2). FIG. 1C shows the DC2 sequence (SEQ ID NO:3). FIG. 1D shows the DC2 collagen domain sequence (SEQ ID NO:4). FIG. 1E shows the ecollagen sequence (SEQ ID NO:5). FIG. 1F shows the ecollagen collagen domain sequence (SEQ ID NO:6). FIG. 1G shows the DC2-3x sequence (SEQ ID NO:7). FIG. 1H shows the DC2-3x collagen domain sequence (SEQ ID NO:8). FIG. 1I shows the DC2-FN sequence (SEQ ID NO:9). FIG. 1J shows the DC2-FN collagen domain sequence (SEQ ID NO:10). FIG. 1K shows the DC2-Thrombin sequence (SEQ ID NO:11). FIG. 1L shows the DC2-Thrombin collagen domain sequence (SEQ ID NO:12). FIG. 1M shows the DC2-Pepsin sequence (SEQ ID NO:13). FIG. 1N shows the DC2-Pepsin collagen domain sequence (SEQ ID NO:14). FIG. 1O shows the DC1-DDR1 sequence (SEQ ID NO:15). FIG. 1P shows the DC1-DDR1 collagen domain sequence (SEQ ID NO:16).

DETAILED DESCRIPTION OF THE INVENTION

Figure 2:
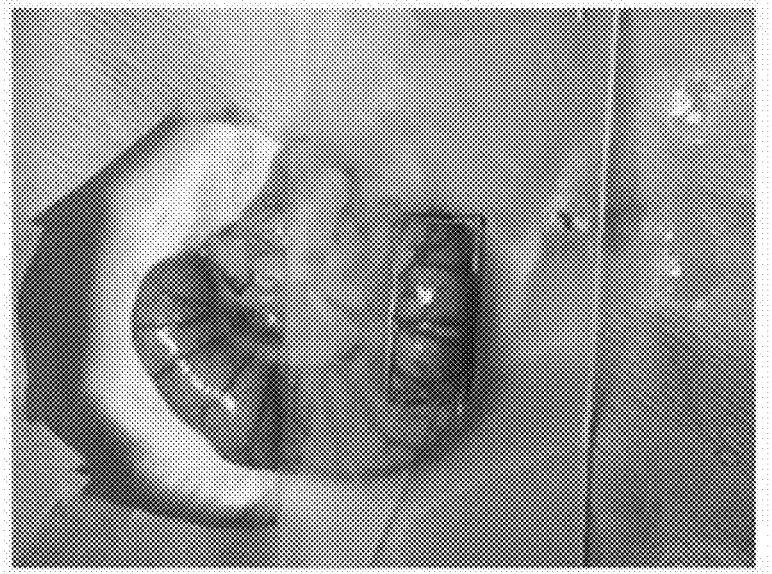
FIGS. 2 and 3 are images of the surgery and results obtained using the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "biocompatible" is a substance that has no medically unacceptable toxic or injurious effects on function.

As used herein, the expression "preventing adhesion formation" is intended to encompass not only the complete elimination of adhesions, but the substantial reduction in the amount or number or complexity of adhesions formed as compared to the amount or number of adhesions formed using a control substance such as saline, or the absence of any treatment to reduce the level of adhesions.

As used herein, "fusion protein" or "synthetic protein" are used interchangeably to refer to proteins created through the joining of two or more genes or gene fragments which originally coded for separate proteins (including peptides and polypeptides). Translation of the fusion gene results in a single protein with functional properties derived from each of the original proteins.

The synthetic or fusion protein for preventing adhesion or fibrosis of the present invention can be administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the synthetic or fusion protein may be formulated to provide, e.g., maximum and/or consistent dosing for the particular form for oral, rectal, topical, intravenous injection or parenteral administration. While the synthetic or fusion protein may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference, and the like, relevant portions incorporated herein by reference.

Liquid dosage forms for administration at a surgical site or to prevent fibrosis may also include, water, a suitable oil, saline, aqueous dextrose (e.g., glucose, lactose and related sugar solutions) and glycols (e.g., propylene glycol or polyethylene glycols) may be used as suitable carriers for liquid solutions. Solutions for administration to a surgical site or a fibrosis include generally, a water-soluble salt of the active ingredient, suitable stabilizing agents, and if necessary, buffering salts. Antioxidizing agents such as sodium bisulfate, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company, a standard reference text in this field, relevant portions incorporated herein by reference.

For direct delivery to the body passages such as nasal passages, sinuses, mouth, throat, esophagus, trachea, lungs and alveoli, the synthetic or fusion protein for preventing adhesion or fibrosis of the present invention may also be delivered as an intranasal form via use of a suitable vehicle. For dermal and transdermal delivery, the synthetic or fusion protein for preventing adhesion or fibrosis of the present invention may be delivered using lotions, creams, oils, elixirs, serums, transdermal skin patches and the like, as are well known to those of ordinary skill in that art. Parenteral forms may also include pharmaceutically acceptable salts and/or minerals and other materials to make them compatible with the type of injection or delivery system chosen, e.g., a buffered, isotonic solution.

Kits. The present invention also includes pharmaceutical kits useful, for example, for the treatment of cancer, which comprise one or more containers containing a pharmaceutical composition comprising a therapeutically effective amount of the synthetic or fusion protein for preventing adhesion or fibrosis of the present invention. Such kits may further include, if desired, one or more of various conventional pharmaceutical kit components, such as, for example, containers with one or more pharmaceutically acceptable carriers, additional containers, etc., as will be readily apparent to those skilled in the art, and/or liquids or solutions such as saline or other physiologically acceptable carrier. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

The synthetic or fusion protein for preventing adhesion or fibrosis of the present invention can be used to prevent adhesion following any surgical procedure. Non-limiting examples of surgical procedures for use of the present invention includes open surgery, minimally invasive surgery, hernia, open-heart surgery, surgery of a ligament, meniscus, patella, mouth sores and oral lesions, tissue bone regeneration, periodontal regeneration, oral reconstruction, vestibuloplasty, tissue regeneration around dental implants, esophagus reconstruction, plastic surgery, cosmetic surgery, peripheral arterial disease, ladder reconstruction, orbital floor repair, treatment of ulcers, corneal repair, adhesion in spinal implant procedures, adhesion in general surgery, vascular conduits, gingival, genitourinary reconstruction, celioscopy, nasoscopy, laryngoscopy, endoscopy, or laparoscopy. Non-limiting examples of fibrosis that can be reduced or prevented using the present invention include a fibrosing disease, scleroderma, pulmonary fibrosis, asthma, keloid scarring, rheumatoid arthritis, lupus, nephrogenic fibrosing dermopathy, fibrotic lesions formed after *Schistosoma japonicum* infection, autoimmune diseases, Lyme disease, stromal remodeling in pancreatitis and stromal fibrosis, chronic obstructive pulmonary disease, uterine fibroids, ovarian fibrosis, other fibrocystic formations, corneal fibrosis or other eye fibrosis, such as that resulting from corneal refraction surgery, fibrosis resulting from congestive heart failure and other post-ischemic conditions, abdominal adhesions, wide angle glaucoma trabeculotomy, and any combinations thereof. Typically, the fusion protein will be provided in sterile form, e.g., lyophilized, gel, hydrogel, or dissolved in a biocompatible liquid or buffer, and the fusion protein can be placed at the location of the possible adhesion or fibrosis (e.g., between tissues that would otherwise adhere), or even be used to irrigate the location after surgery.

The present invention can be used alone or in combination with one or more biologically active agents. For example, the fusion protein that eliminates tissue adhesion or fibrosis of the present invention can be combined with the following non-limiting examples of agents: amoxicillin, ampicillin, azlocillin, aztreonam, azithromycin, bacitracin, bifonazole, butoconazole, butenafine, colistin, carbomer, cyclosporin, carmellose, carbenicillin, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, chloramphenicol, ciprofloxacin, cilastatin, clindamycin, clarithromycin, cloxacillin, clotrimazole, dicloxacillin, doxycycline, dirithromycin, dextran, demeclocycline, ertapenem, ethambutol, erythromycin, fenticonazole, fosfomycin, fusidic acid, furazolidone, flucytosine, fluconazole, gatifloxacin, griseofulvin, gentamicin, gentian violet, haloprogin, herimycin, hyaluronic acid, itraconazole, kanamycin, neomycin, netilmicin, streptomycin, tobramycin, paromomycin, loracarbef, lincoamycin, isoniazid, linezolid, metronidazole, meropenem, teicoplanin, vancomycin, roxithromycin, troleandomycin, telithromycin, spectinomycin, flucloxacillin, mezlocillin, minocycline, nafcillin, oxytetracycline, oxiconazole, penicillin, peperacillin, polymyxin B, enoxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, tetracycline, mupirocin, nitrofurantoin, platensimycin, pyrazinamide, quinupristin/dalfopristin, rifampin/rifampicin, tinidazole, ticarcillin, miconazole, ketoconazole, econazole, isoconazole, sertaconazole, sulconazole, tioconazole, ravuconazole, posaconazole, voriconazole, teronazole, terbinafine, tolnaftate, or undecylenic acid. Other non-limiting examples of active agents for use with the fusion protein of the present invention include: a steroidal anti-inflammatory agent, analgesic, sedative, tranquilizer, steroid, antispasmodic, antihistamine, antihypertensive agent, antiviral, oligonucleotide(s), carbohydrate(s), anti-ageing agents, anti-oxidants, vitamins, minerals, and any combination thereof.

The fusion protein that eliminates tissue adhesion or fibrosis of the present invention can also form part of a coating, e.g., when mixed with or used to coat or cover a medical device. The present invention can be combined with polymeric matrix that comprises a biodegradable polymer, a non-biodegradable polymer, a mixture of biodegradable and non-biodegradable polymers, or a copolymer comprising biodegradable and non-biodegradable units, or a physiological buffer (e.g., when sprayed on the tissue, the device, or both). Non-limiting examples of biodegradable polymers can include: poly(lactide), poly(glycolide), poly(lactide-co-glycolide), poly(lactic acid), poly(glycolic acid), poly(lactic acid-co-glycolic acid), polyanhydride, polyorthoester, polyetherester, polycaprolactone, polyesteramide, block copolymers of polyethylene glycol and lactide or glycolide, and blends and copolymers thereof. Non-limiting examples of non-biodegradable polymer can include: non-biodegradable polyacrylate, polymers of ethylene-vinyl acetate, polymers of acyl-substituted cellulose acetate, non-degradable polyurethane, polystyrene, polyvinyl chloride, polyvinyl fluoride, poly(vinyl imidazole), chlorosulphonate polyolefin, polyethylene oxide, and blends and copolymers thereof. For example, the present invention can be sprayed on, or coated on needles, guide wires, catheters, surgical instruments, equipment for endoscopy, wires, stents, angioplasty balloons, wound drains, wound dressings, arteriovenous shunts, gastroenteric tubes, urethral inserts, laparoscopic equipment, pellets, and/or implants.

Thus, in at least one example, the present invention includes a biocompatible formulation comprising a fusion protein comprising an isolated and purified triple helical bacterial backbone protein that reduces or eliminates postoperative adhesions and one or more triple helix forming peptide motifs that show a reduced adhesion, wherein the fusion protein reduces or eliminates postoperative adhesions and one or more biocompatible agents.

The fusion protein of the present invention can also include as motifs amino acid sequences, such as, e.g., one or more binding motifs that comprise an integrin(s) binding site, a matrix metalloproteinase (MMP) binding site, a discoidin domain-containing receptor (DDR) binding site, a fibronectin binding site, a bone sialoprotein binding site, a decorin binding site, a fibromodulin binding site, a lumican binding sites, heparin, or other binding sites added to the fusion protein, which are well-known in the art. One or more of these peptide motifs can be inserted into the non-thrombogenic bacterial or viral collagen using techniques well-known in the molecular biology arts as taught in, e.g., Sambrook et al., Molecular Cloning: A Laboratory Manual New York: Cold Spring Harbor Laboratory Press, 2012, relevant portions incorporated herein by reference.

Non-limiting examples of sources for non-thrombogenic bacterial collagen include, but are not limited to, *Streptococcus, Bacillus, Legionella, Clostridium, Solibacter, Rhodopseudomonas, Methylobacterium*, or other bacterial and viral collagens. Other examples of such collagens are taught by, Yu, et al., Bacterial collagen-like proteins that form triple-helical structures, J Struct Biol. 2014 June; 186(3):451-461, and Rasmussen, et al., Genome-based Identification and Analysis of Collagen-related Structural Motifs in Bacterial and Viral Proteins, J. Biol. Chem., Vol. 278, No. 34, Issue of August 22, pp. 32313-32316, 2003, relevant sequences incorporated herein by reference.

Thus, in one embodiment of the present invention, there is provided a recombinant or synthetic collagen. This recombinant collagen contains a triple helical backbone protein produced in a prokaryotic expression system, such as those taught by Yu, et al., (supra), and in the present application. Typically, the protein contains at least one 'inserted' biologically active sequence(s). In one form, the recombinant synthetic collagen has a triple helical backbone derived from a Streptococcal or other bacterial protein. In another form, the Streptococcal protein contains a collagen-like repeat of GXYGX1Y1GX2Y2GXY (SEQ ID NO:17) and wherein the recombinant synthetic collagen is created by changing X1 position to L, R, or F residues or Y2 position to R, K, or N residues. In one preferred form, the biologically active sequence is an integrin binding motif. Generally, the recombinant synthetic collagen of the present invention are capable of binding to integrins α1β1 and/or α2β1 without hydroxyproline.

In the recombinant synthetic collagen of the present invention, representative biologically active sequences are GLPGER (SEQ ID NO:18), GLPGEN (SEQ ID NO:19), GLPGEK (SEQ ID NO:20), GRPGER (SEQ ID NO:21), GRPGEN (SEQ ID NO:22), GRPGEK (SEQ ID NO:23), GFPGER (SEQ ID NO:24), GFPGEN (SEQ ID NO:25), or GFPGEK (SEQ ID NO:26). In one form, the recombinant synthetic collagen of the present invention is produced in a bacterial expression system deficient in post-translational modification.

Particularly, in a related embodiment, the present invention therefore provides the specific biologically active motif sequences of the recombinant synthetic collagen shown in GLPGER (SEQ ID NO:18), GLPGEN (SEQ ID NO:19), GLPGEK (SEQ ID NO:20), GRPGER (SEQ ID NO:21), GRPGEN (SEQ ID NO:22), GRPGEK (SEQ ID NO:23), GFPGER (SEQ ID NO:24), GFPGEN (SEQ ID NO:25), and GFPGEK (SEQ ID NO:26).

As is described in detail infra, the recombinant synthetic collagen of the present invention may be designed to have a variety of functions. For example, the collagen containing sequences GLPGER (SEQ ID NO:18), GRPGER (SEQ ID NO:21), or GFPGER (SEQ ID NO:24)), support adherence of both α1β1 and α2β1, spreading of endothelial cells, fibroblasts, chondrocytes, and smooth muscle cells. Also, the collagen containing sequence GFPGER (SEQ ID NO:24) support adherence and spread of mesenchymal stem cells and adipocyte stem cells. In addition, the collagen containing sequences GFPGER (SEQ ID NO:24) and GFPGEN (SEQ ID NO:25) support adherence and spread of mesenchymal stem cells.

In one embodiment, the present invention provides a recombinant synthetic collagen containing a GFPGEN (SEQ ID NO:11) sequence selectively bind to integrin α1β1, but not to α2β1. This recombinant synthetic collagen supports adherence of endothelial cells, fibroblasts, and chondrocytic cells, but does not support adherence of smooth muscle cells.

In another embodiment, the present invention provides a recombinant synthetic collagen containing GLPGER (SEQ ID NO:4), GRPGER (SEQ ID NO:7), GFPGER (SEQ ID NO:10), or GFPGEN (SEQ ID NO:11) sequences. Such recombinant synthetic collagens do not aggregate platelets and are non-thrombogenic.

In another embodiment, the present invention provides a recombinant synthetic collagen containing a GFPGER (SEQ ID NO:10) sequence. Such a recombinant synthetic collagen inhibits collagen-induced platelet aggregation. In another embodiment, the present invention provides a recombinant synthetic collagen containing a GFPGEN (SEQ ID NO:11) sequence. Such a recombinant synthetic collagen does not inhibit collagen-induced platelet aggregation. In another embodiment, the present invention provides a recombinant synthetic collagen containing one, two, three, four and/or five multiple cell binding motifs. Such recombinant synthetic collagens have a density dependent increase in integrin affinity, cell binding, and cell migration. In another embodiment, the present invention provides a recombinant synthetic collagen containing one, two, three, four and/or five GLPGER (SEQ ID NO:18) cell binding motifs.

In another embodiment, the present invention provides a recombinant synthetic collagen wherein said collagen is affixed to or linked in a chemical manner to a scaffold with intrinsic tensile properties. A person having ordinary skill in this art would readily recognize useful scaffolds but representative examples include but are not limited to PEG-containing hydrogels, ECM components, and mesh materials.

In another embodiment, the present invention provides a recombinant synthetic collagen containing a triple helical backbone protein produced in a prokaryotic expression system. In another embodiment, the present invention provides a recombinant synthetic collagen further comprising an insert selected from the group consisting of but not limited to bone sialoprotein binding sequences, von Willibrand factor, integrins α10β1 and α11β1 binding sequences, heparin, fibronectin, and an extracellular matrix constituent.

The following example(s) are given for the purpose of illustrating various embodiments of the invention and are not meant to limit the present invention in any fashion.

Example 1

Designer Collagens produced in a bacterial expression system bind to integrin α1β1 and/or α2β1 and as substrates support adherence and spreading of multiple cell types.

Post-translational modification of collagen to include hydroxyproline residues is important to stabilize the triple helical conformation of collagen. Hydroxyproline has also been implicated in collagen binding to integrins, including α1β1 and α2β1. For example, unhydroxylated collagen produced in plants shows reduced binding affinity for integrin α1β1 and failed to bind α2β1. Adhesion of platelets on unhydroxylated collagen via integrin α2β1 is weaker than on hydroxylated collagen and unhydroxylated collagen fails to induce platelet aggregation. This data suggests that hydroxyproline on collagen is essential for high affinity binding to α1β1 and α2β1. A molecular mechanism detailing the binding differences of unhydroxylated and hydroxylated collagen to integrins α1β1 and α2β1 is unknown. Therefore, the present invention describes new materials capable of binding to integrins α1β1 and α2β1 without hydroxyproline.

Designer Collagens with 'inserted' biologically active sequences, GLPGER (SEQ ID NO:18), GLPGEN (SEQ ID NO:19), GLPGEK (SEQ ID NO:20), GRPGER (SEQ ID NO:21), GRPGEN (SEQ ID NO:22), GRPGEK (SEQ ID NO:23), GFPGER (SEQ ID NO:24), GFPGEN (SEQ ID NO:25), GFPGEK (SEQ ID NO:26), were produced in a bacterial expression system, which is deficient in post-translational modification, including hydroxylation of proline and lysine residues. Designer Collagens with 'inserted' sequences (GLPGER (SEQ ID NO:18), GRPGER (SEQ ID NO:21), and GFPGER (SEQ ID NO:24)), however, support adherence of both α1β1 and α2β1 regardless of the lack of hydroxyproline. This conclusion was reached by ELISA-based assays and Surface Plasmon Resonance analysis. Since many cell types express α1β1 and α2β1, Designer Collagens support adherence and spreading of different cell types including endothelial cells, fibroblasts, chondrocytes, and smooth muscle cells. Cell adherence was quantified and cell morphology was evaluated using fluorescence microcopy techniques.

Example 2

Designer Collagens with a GFPGEN (SEQ ID NO:25) residue sequence selectively bind to integrin α1β1, but not to α2β1. Selective binding was determined by ELISA-based assays and Surface Plasmon Resonance analysis. The Designer Collagen with GFPGEN (SEQ ID NO:25) as a substrate supports adherence of endothelial cells, fibroblasts, and chondrocytic cells, but does not support adherence of smooth muscle cells.

Example 3

The Designer Collagens are non-thrombogenic. Collagen is one of several agonists that can activate platelets by the binding of specific sequences, GFOGER (SEQ ID NO:1) and/or GLOGER (SEQ ID NO:2), to integrin α2β1 on platelets. Designer Collagens with residue motifs GLPGER (SEQ ID NO:18), GRPGER (SEQ ID NO:21), GFPGER (SEQ ID NO:24), and GFPGEN (SEQ ID NO:25) were tested in platelet aggregation assays to determine whether they activate platelets. Designer Collagens do not aggregate platelets at 10-fold higher concentrations than native collagen in platelet aggregation assays. This data indicates that these Designer Collagens are completely non-thrombogenic although they contain sequences that are derived from native collagen, which act as an agonist for platelet aggregation.

Designer Collagens were tested in platelet aggregation inhibition assays to determine whether they can inhibit collagen-induced platelet aggregation. Designer Collagens with GFPGER (SEQ ID NO:24) inhibits collagen-induced platelet aggregation indicating that Designer Collagens with GFPGER (SEQ ID NO:24) competes with native collagen to bind α2β1 without aggregating platelets. The Designer Collagen with GFPGER (SEQ ID NO:24) is an antagonist to inhibit collagen-induced platelet aggregation via the blocking of α2β1 integrin. The Designer Collagen with a GFPGEN (SEQ ID NO:25) residue sequence did not inhibit collagen-induced platelet aggregation since the Designer Collagen only binds to integrin α2β1 that is not normally expressed on platelets. The Designer Collagen with GFPGEN (SEQ ID NO:25) would be an ideal biomaterial for vascular applications.

The introduction of one, two, three, four and/or five multiple cell binding motifs results in a density dependent increase in integrin affinity, cell binding, and cell migration. This was determined by comparing Designer Collagens with one, two, three, four and five GLPGER cell binding motifs. Integrin affinity was assessed by surface plasmon resonance. Cell binding and migration was demonstrated with human umbilical vein endothelial cells.

Example 4

Construction of Designer Collagens. Bacterial collagen-like proteins derived from Group A *Streptococcus* have been used as a template to produce Designer Collagens with inserted motifs with specific functions. The functional motifs have receptor binding activities through an interaction with collagen binding integrins, α1β1 and α2β1. These proteins are termed Designer Collagens and they include the following characteristics: humanized collagen fragments or fragments generated through computer modeling that are inserted into a bacterial collagen-like backbone and produced in a prokaryotic expression system. pSL163, a collagen-like protein from Group A *Streptococcus* was used as a template to insert receptor-binding motifs. Site-directed mutagenesis was performed to change X1 position to L, R, or F residues or and X2 position to R, K, or N residues (FIG. 1). These constructs were expressed in *E. coli* and recombinant proteins were purified. The library of Designer Collagens contains recombinant proteins with the following receptor-binding motifs: GLPGER (SEQ ID NO:18), GRPGER (SEQ ID NO:21), GFPGER (SEQ ID NO:24), GLPGEN (SEQ ID NO:19), GRPGEN (SEQ ID NO:22), GFPGEN (SEQ ID NO:25), GLPGEK (SEQ ID NO:26), GRPGEK (SEQ ID NO:23), and GFPGEK (SEQ ID NO:26). The present invention characterized the identity and purity of these recombinant proteins using SDS-PAGE, Western-blot analysis, and Circular Dichroism spectroscopy. All of these proteins formed a triple helical structure. The binding of the Designer Collagens with residue sequences of GLPGER (SEQ ID NO:18), GRPGER (SEQ ID NO:21), GFPGER (SEQ ID NO:24), GLPGEN (SEQ ID NO:19), GRPGEN (SEQ ID NO:22), GFPGEN (SEQ ID NO:25), GLPGEK (SEQ ID NO:26), GRPGEK (SEQ ID NO:23), and GFPGEK (SEQ ID NO:26), to α1 and α2 I domains were examined in ELISA-based assays. The binding of Designer Collagens with residue sequences of GFPGER (SEQ ID NO:24), GRPGER (SEQ ID NO:21), GLPGER (SEQ ID NO:18), and GFPGEN (SEQ ID NO:25) was tested using Surface Plasmon Resonance analysis using a BIAcore 3000 machine. C2C12 cells, derived from a mouse myoblast cell line, lack expression of the α-subunit of collagen binding integrins α1β1, α2β1, α10β1, and α11β1. These cells can be utilized to determine the individual contribution of integrin binding to a substrate. The a subunits are stably expressed in individual cells line, C2C12-α1 and C2C12-α2. Whether immobilized Designer Collagens in the library support adherence and spreading of these cell types was tested. In addition, endothelial cells, fibroblasts, chondrocytic cells, and smooth muscle cells were tested in adherence and spreading assays. The ability of cells to migrate on immobilized Designer Collagens in 96 well plates, tissue culture chamber slides, or modified migration assays plates was determined. The Designer Collagens were also tested in platelet aggregation assays to determine whether the Designer Collagens bind and activate platelets.

Based on the experimental data, proteins with unique and novel characteristics were demonstrated. The Designer Collagen with GFPGEN (SEQ ID NO:25) residues is a biomaterial for vascular applications. The Designer Collagen with GFPGER (SEQ ID NO:24) residues is an antagonist, which blocks interaction of collagen with α2β1 on platelets. The Designer Collagen with GFPGER (SEQ ID NO:24) residues can interact with α1α1 and α2β1 and therefore may be a cell recruiting molecule with applications in angiogenesis, wound healing, and orthopedics.

Designer Collagens need to be biocompatible and non-immunogenic in humans, which will be addressed using appropriate animal models before clinical trials. Modification of certain portions of Designer Collagen may be required for appropriate use in humans. Designer Collagens are proteins that do not naturally form higher ordered structures such as fibers; therefore, Designer Collagens lack intrinsic tensile properties or a three-dimensional structure. Designer Collagens may need to be affixed to or linked in a chemical manner to a scaffold with intrinsic tensile properties. Currently, PEG-containing hydrogels, ECM components, and mesh materials may be used as scaffolds.

Example 5

Recombinant Designer Collagens expressed in a bacterial system exhibit a triple helical structure at physiological temperatures. pSL163 (P163), a construct containing bacterial collagen-like sequences that form a triple helix, was used as a backbone. To generate receptor-binding motifs including, GLPGER (SEQ ID NO:18), GLPGEN (SEQ ID NO:19), GLPGEK (SEQ ID NO:20), GRPGER (SEQ ID NO:21), GRPGEN (SEQ ID NO:22), GRPGEK (SEQ ID NO:23), GFPGER (SEQ ID NO:24), GFPGEN (SEQ ID NO:25), GFPGEK (SEQ ID NO:26), site-directed mutagenesis was used to 'insert' these cell-binding sites into the pSL163 backbone (FIG. 1). The constructs were expressed in E. coli and recombinant proteins were purified. As shown in FIG. 2A, purified collagen-like proteins have over 95% purity and form a triple helical structure under non-denatured conditions in 12% SDS-PAGE. Residue sequences correspond to the following numbered system (1-GLPGER (SEQ ID NO:18), 2-GLPGEN (SEQ ID NO:19), 3-GLPGEK (SEQ ID NO:20), 4-GRPGER (SEQ ID NO:21), 5-GRPGEN (SEQ ID NO:22), 6-GRPGEK (SEQ ID NO:23), 7-GFPGER (SEQ ID NO:24), 8-GFPGEN (SEQ ID NO:25), 9-GFPGEK (SEQ ID NO:26)). Far UV Circular Dichroism spectral data recorded with wavelength scans of the Designer Collagens showed a typical triple helical structure (FIGS. 2B-2J). Circular Dichroism scans were recorded at 220 nm with a temperature slope of 10 degrees Celsius per hour. This data demonstrated that the Designer Collagens maintain a triple helical structure at a temperature close to normal human body temperature (FIGS. 2K-2S).

Example 6

Figure 3:
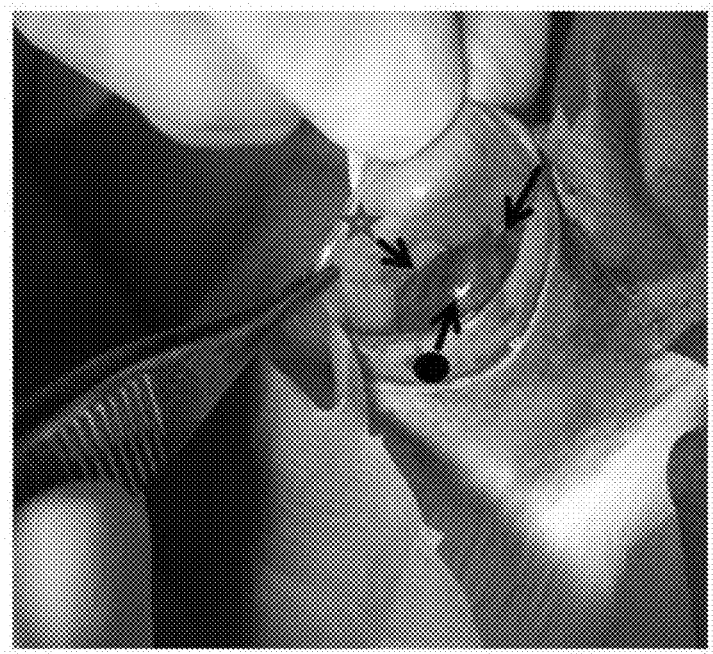
Figure 4A:
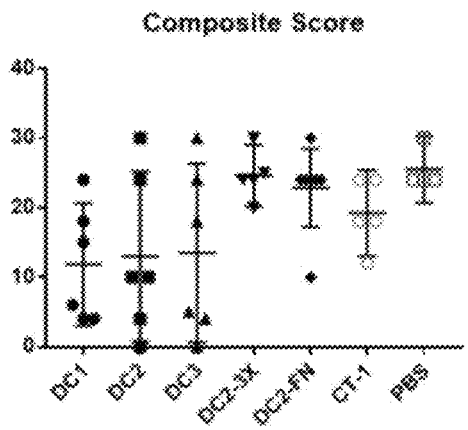
FIGS. 4A-4E are scatter plots with mean and 95% CI of each of the variables shown.
Figure 4B:
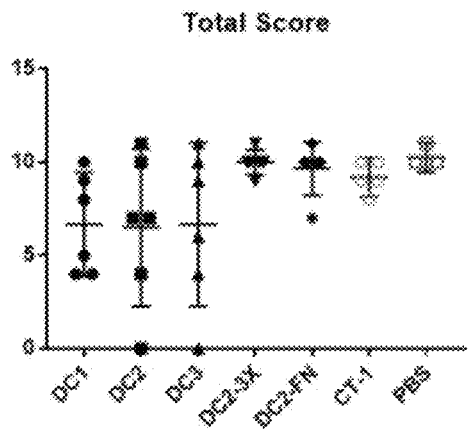
Figure 4C:
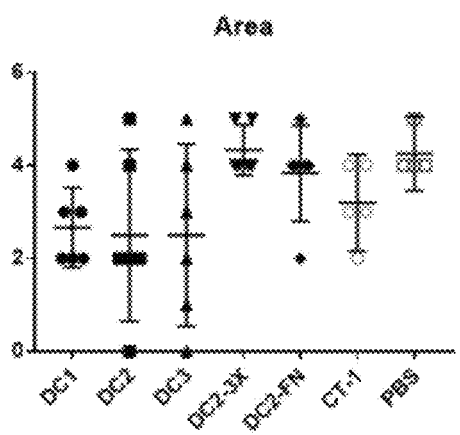
Figure 4D:
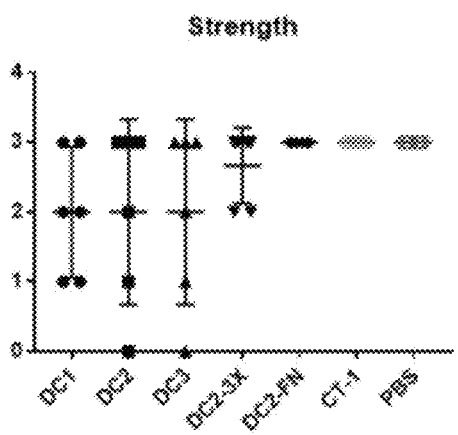
Figure 4E:
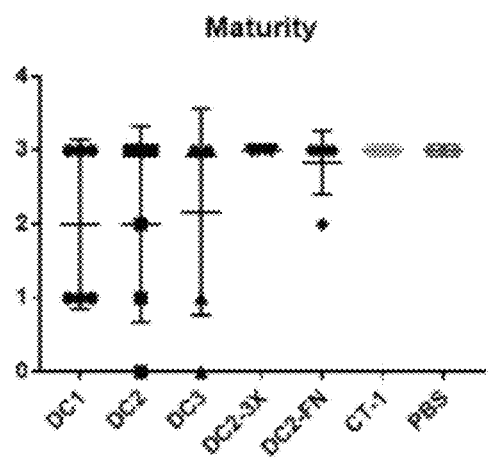

Integrins interact with Designer Collagens containing GLPGER (SEQ ID NO:18), GLPGEN (SEQ ID NO:19), GLPGEK (SEQ ID NO:20), GRPGER (SEQ ID NO:21), GRPGEN (SEQ ID NO:22), GRPGEK (SEQ ID NO:23), GFPGER (SEQ ID NO:24), GFPGEN (SEQ ID NO:25), and GFPGEK (SEQ ID NO:26) cell-binding inserts. Binding of recombinant forms of integrins α1 and α2 I domains to immobilized Designer Collagens with GLPGER (SEQ ID NO:18), GLPGEN (SEQ ID NO:19), GLPGEK (SEQ ID NO:20), GRPGER (SEQ ID NO:21), GRPGEN (SEQ ID NO:22), GRPGEK (SEQ ID NO:23), GFPGER (SEQ ID NO:24), GFPGEN (SEQ ID NO:25), and GFPGEK (SEQ ID NO:26), motifs were determined by ELISA-based assays (FIGS. 3A-3B and FIGS. 4A-4B). Binding of recombinant forms of integrins α1 and α2 I domains to immobilized Designer Collagens with GRPGER (SEQ ID NO:21), GLPGER (SEQ ID NO:18), and GFPGER (SEQ ID NO:24), was determined by Surface Plasmon Resonance analysis (FIGS. 5C and 5D-5F). The Designer Collagens with GLPGER (SEQ ID NO:18), GRPGER (SEQ ID NO:21), and GFPGER (SEQ ID NO:24) support the binding of α1 and α2 I domains (FIGS. 4A-4B, grey bars) via a metal ion dependent manner since binding is completely abolished by EDTA (FIGS. 4A-4B, white bars). C2C12 cells stably expressing either integrin α1 or α2 subunit (C2C12-α1 or C2C12-α2) were used to determine whether the Designer Collagens with GLPGER (SEQ ID NO:18), GRPGER (SEQ ID NO:21), and GFPGER (SEQ ID NO:24) motifs support adhesion of these cell lines.

As shown in FIG. 5A, the Designer Collagens allowed adherence of C2C12-a1 cells or C2C12-α2 cells at a similar level of adherence to collagen type I, a positive control. Because pSL163 is a Designer Collagen without an 'inserted' motif, it is used as a negative control and did not mediate adherence of either cell type. This is an invaluable control because it implicates specific sequences are responsible for the interactions and not solely the presence of a triple helical protein. C2C12 parental cells did not adhere on any substrates; indicating the adhesion of C2C12-α1 and C2C12-α2 cells to the Designer Collagens is mediated by integrin α1β1 and α2β1. Cell adherence to substrates via specific integrins will exhibit outside-in signaling to induce intracellular signaling pathways, which will manifest as a morphology change resulting in spreading of cells. Adhered C2C12-α1 and C2C12-α2 cells on the Designer Collagens exhibited spreading within 60 minutes incubation at 37° C. in the presence of 5% $CO_2$ (FIG. 5B). This indicates that integrin binding motifs, GLPGER (SEQ ID NO:18), GRPGER (SEQ ID NO:21), and GFPGER (SEQ ID NO:24) actively bind to cells and induce intracellular signaling pathways. In addition, the Designer Collagens allow attachment and spreading of different cell types including endothelial cells in a dose-dependent manner (FIG. 5C), fibroblasts (MRC5), smooth muscle cells, and chondrocytic cells (SW1353) (FIGS. 5D-5F). FIG. 5D shows that the Designer Collagens allow attachment and spreading of endothelial cells in a dose-dependent manner. FIGS. 5E-5G show that the Designer Collagens allow attachment and spreading of fibroblasts (MRC5), smooth muscle cells, and chondrocytic cells (SW1353) in a dose-dependant manner.

Example 7

Designer Collagens with GLPGER (SEQ ID NO:18), GRPGER (SEQ ID NO:21), and GFPGER (SEQ ID NO:24) motifs are non-thrombogenic. The Designer Collagens support adherence of different cell types, some through an interaction with α2β1. Thus, whether Designer Collagens activated platelets by binding to integrin α2β1 was examined. FIG. 6 shows that Designer Collagens did not induce platelet aggregations at a 10-fold higher concentration than collagen type I, which aggregates platelets to over 90% in 10 minutes.

Example 8

Designer Collagen with an inserted motif of GFPGEN (SEQ ID NO:25) selectively binds to integrin 11, but not to 21. The Designer Collagen with a GFPGEN (SEQ ID NO:25) motif was expressed in E. coli and purified. It was tested for binding to integrin 1 and 2 I domains by ELISA based assays and Surface Plasmon Resonance analysis. The integrin 1 I domain binds to immobilized GFPGEN (SEQ ID NO:25) containing Designer Collagen, while the integrin 2 I domain fails to bind to Designer Collagen containing GFPGEN (SEQ ID NO:25) motifs (FIG. 7A). Integrin 1 and 2 I domains bind to immobilized GFPGER (SEQ ID NO:24) containing Designer Collagen and collagen type I as shown previously. In cell adherence assays, C2C12-1 cells only adhere on GFPGEN (SEQ ID NO:25) containing Designer Collagen, but C2C12-2 cells and C2C12 parental cells do not (FIG. 7B), this indicates that GFPGEN (SEQ ID NO:25)

selectively interacts with integrin 11. The interaction of integrin 11 with GFPGEN (SEQ ID NO:25) induces intracellular signaling as shown by spreading of C2C12-1 cells on a GFPGEN (SEQ ID NO:25) containing Designer Collagen (FIG. 7C). GFPGEN (SEQ ID NO:25) containing Designer Collagen also supported adhesion and spreading of human endothelial cells (FIG. 7D, where GFPGXY (SEQ ID NO:27) is GFPGEN (SEQ ID NO:25), HUVEC graph). GFPGEN (SEQ ID NO:25) containing Designer Collagen did not support the adherence of smooth muscle cells (SMC) (FIG. 7D, where GFPGXY (SEQ ID NO:27) is GFPGEN (SEQ ID NO:25), SMC graph). Integrin 21 is expressed on endothelial cells as well as smooth muscle cells.

Intracellular pathways activated upon cell adherence to Designer Collagens with inserted motifs of GFPGER (SEQ ID NO:24) and GFPGEN (SEQ ID NO:25) were determined herein. Activation of focal adhesion kinase (FAK) was detected in human dermal microvascular endothelial cells lysate 30 minutes after adherence to Designer Collagens and Collagen type 1, but not P163 as demonstrated by Western blot analysis (FIGS. 8A-8F). Binding and oligomerization of both α1 and α2 in complex with α1 leads to autophosphorylation of Y397. Therefore, the results demonstrated by activation of FAK pY397 by Collagen type 1 and Designer Collagens show Designer Collagen not only bind to integrins, but mediate intracellular signaling. Collagen type 1 will preferentially bind α2 when both ligands are available. α2 signaling does not activate Shc, however it activates p38. Results herein indicate a strong activation of Shc by GFPGEN (SEQ ID NO:25) containing Designer Collagen, an activation of Shc by GFPGER (SEQ ID NO:24) containing Designer Collagen, and minimal to no activation of Shc by Collagen type 1. The results also indicate a strong activation of p38 by Collagen type 1, activation of p38 by GFPGER (SEQ ID NO:24) containing Designer Collagen, and minimal to no activation by GFPGEN (SEQ ID NO:25) containing Designer Collagen.

The data shown indicates reproducible and predictable activation signals by Collagen type 1. However, GFPGER (SEQ ID NO:24) containing Designer Collagen despite the capability of binding both α1 and α2 does not activate Shc or p38 in the same manner as Collagen type 1. These data suggest a more equal preference of GFPGER (SEQ ID NO:24) containing Designer Collagen to bind α1 and α2 when compared to Collagen type 1. These intracellular signaling properties add to the usefulness of Designer Collagens mediating specific cell functions such as angiogenesis, wound healing, adhesion prevention, cell recruitment, cell proliferation, and cell death.

Example 9

Designer collagen with a GFPGEN (SEQ ID NO:25) motif is non-thrombogenic. The Designer Collagen with a GFPGEN (SEQ ID NO:25) motif is non-thrombogenic as shown in platelet aggregation assays (FIG. 6). Since GFPGEN (SEQ ID NO:25) only binds to integrin α1β1, while GFPGER (SEQ ID NO:24) binds to both integrin α1β1 and α2β1, whether GFPGER (SEQ ID NO:24) and GFPGEN (SEQ ID NO:25) could inhibit collagen-induced platelet aggregations was examined. GFPGER (SEQ ID NO:24) shows inhibitory effects on collagen type I induced platelet aggregation. This indicates that the Designer Collagen binds to integrin α2β1 on platelets without activation and competitively blocks the binding of native collagen type I (FIG. 9). GFPGEN (SEQ ID NO:25) containing Designer Collagen did not inhibit collagen induced platelet aggregation, indicating that GFPGEN (SEQ ID NO:25) does not compete with native collagen type I for the binding to integrin α2β1 on platelets. It is known that integrin α1β1 is not expressed on platelets.

Example 10

Cell adhesion and migration is modulated by density and affinity of integrin specific motifs on the Designer Collagen substrates. Whether modulation of density and affinity of integrin specific motifs on the Designer Collagen would influence cell behavior including attachment and migration on the substrates was determined. To this end, P163 was used to present spatial multiple integrin binding repeats that contain one, two, three, four or five repeats of GLPGER (SEQ ID NO:18) sequences. GXY repeat sequences are located between the GLPGER (SEQ ID NO:18) repeats to provide space between the integrin specific motifs (GLPGER-1 (SEQ ID NO:18), GLPGER-2 (SEQ ID NO:18), and GLPGER-3 (SEQ ID NO:18)) (FIG. 10A). The Designer Collagens form oligomers on a polyacrylamide gel under non-reducing condition and also exhibited a typical triple helix structure with melting temperature values of 36.5° C. in thermal transition analyzed by CD spectroscopy. Surface Plasmon Resonance analysis was performed by passing over I domains to immobilized GLPGER-1 (SEQ ID NO:18), GLPGER-2 (SEQ ID NO:18), and GLPGER-3 (SEQ ID NO:18). The results indicated that α1 I and α2 I domains bound to the Designer Collagens in the presence of 1 mM MgCl2 (FIG. 10B, where Y axis is α1 I domain and 11c, where Y axis is α2 I domain) and the binding was abolished in the presence of 1 mM EDTA. Normalized representative binding profiles of the I domains to captured GLPGER-1 (SEQ ID NO:18), GLPGER-2 (SEQ ID NO:18), and GLPGER-3 (SEQ ID NO:18) resulted in an increased in the binding affinity of the I domains to Designer Collagens with increased number of GLPGER (SEQ ID NO:18) repeats. The dissociation constant (KD) of integrin α1 I domain to captured GLGPER (SEQ ID NO:18) repeats was 1.33±0.15 µM, while that of integrin α2 I domain was 39.7, 25.9, and 11.8 µM to captured GLPGER-1 (SEQ ID NO:18), GLPGER-2 (SEQ ID NO:18), GLPGER-3 (SEQ ID NO:18), respectively.

To assess the specificity of cell-substrate interactions, cell adhesion to the Designer Collagens was investigated by seeding human endothelial cells in serum-free medium containing 1 mM MgCl2 and 1 mM CaCl2 to 96 wells coated with increased concentration of GLPGER-1 (SEQ ID NO:18), GLPGER-2 (SEQ ID NO:18), GLPGER-3 (SEQ ID NO:18), Collagen type I, and P163. All GLPGER (SEQ ID NO:18) repeats served as a substrate for the attachment of the endothelial cells, as did type I Collagen (FIG. 10C). The attachment of cells depends on surface density of GLPGER (SEQ ID NO:18) contributed from amounts of coated substrates as well as numbers of integrin specific motifs, which give rise to increased attachment of the endothelial cells on the substrates. FIG. 10D shows cell adhesion to the Designer Collagens investigated by seeding human endothelial cells in serum-free medium containing 1 mM MgCl2 and 1 mM CaCl2 to 96 wells coated with increased concentration of GLPGER-1 (SEQ ID NO:18), GLPGER-2 (SEQ ID NO:18), GLPGER-3 (SEQ ID NO:18), Collagen type I, and P163. All GLPGER (SEQ ID NO:19) repeats served as a substrate for the attachment of the endothelial cells, as did type I Collagen.

The effect of ligand density and affinity on endothelial cell migration was determined by counting migrated cells after a 4 hour time period in the presence and absence of soluble Designer Collagens GLPGER-1 (SEQ ID NO:18), GLPGER-2 (SEQ ID NO:18), GLPGER-3 (SEQ ID NO:18), and type I Collagen and P163. These results showed that the integrin specific motifs on Designer Collagens are able to support cell migration in the absence of other cell-substrate adhesive interactions. Increased density and numbers of integrin specific motifs on Designer Collagens resulted in a dramatic increasing of cell migration that reached the highest level in comparison to Collagen type I (FIG. 10E). The endothelial cell migration is enhanced in a dose-dependant manner and controlled by modulating ligand surface density and binding affinity. FIG. 10F shows that Designer Collagens containing 4 and 5 repeats of the integrin binding sequence, GLPGER (SEQ ID NO:18), respectively, bind α1 I domain with increased affinity in comparison to a single GLPGER (SEQ ID NO:18) repeat.

Designer Collagen is prepared as a pathogen-free biomaterial using a prokaryotic expression system. Prokaryotic expression systems can be scaled up with current manufacturing process pipelines and offer lot-to-lot consistency with cost-effectiveness. Designer Collagens have the capacity to form a triple helix without the presence of hydroxyproline, which adds a cost advantage. Designer Collagens have multiple and different inserted sequences, which requires separate production. The mixing of Designer Collagens for product optimization is possible post-purification. A possible limitation of prokaryotic expression is the lack of post-translation modification. Certain applications of Designer Collagens do not require post-translational modification, but if the need arises, alternative expression systems could be used. Current methods of collagen purification rely on purification methods from an animal source. These methods are inconsistent, expensive, and offer only native collagen.

Designer Collagens that do not contain any 'inserted' residue such as, pSL163, showed minimal binding to integrin I domains did not support the adherence of different cell types. Thus, these Designer Collagens could be used as anti-adhesion biomaterials. Anti-adhesion materials currently use cellulose or other coatings of a mesh to prevent the formation of adhesion after trauma or surgery. Designer Collagens containing could be useful in cell recruitment or maintenance of a certain cell type in a localized area. The adherence to and subsequent intracellular signaling of α1β1 and α2β1 by GFPGER (SEQ ID NO:24) containing Designer Collagens could be useful in stimulating multi-step processes such as angiogenesis. Designer Collagens containing GFPGEN (SEQ ID NO:25) could be optimal vascular graft coatings or stent coatings. This unique biomaterial supports the adherence and spreading of endothelial cells but not smooth muscle cells and does not mediate platelet aggregation. Alternative formulations may include chimeric Designer Collagens encompassing different protein domains to achieve a desired function, chemical crosslinking effects needed to instill a certain property with regard to stability, a chemical effect needed to facilitate attachment of Designer Collagens to a certain material, and undetermined 'inserts' which impart a new property and function of Designer Collagens for new markets. These undetermined 'inserts' could range in function, however, other representative targets include bone sialoprotein binding sequences, integrins α10β1 and α11β1 binding sequences, and many extracellular matrix constituents.

Furthermore, additional sequences can include four triplet GRPG-KPGK-QGQK (SEQ ID NO:28) sequences corresponding to the heparin-binding site of collagen, which can also be included in the recombinant collagen fusion proteins of the present invention.

The present invention provides a triple helix protein structure that reduces adhesion formation. In one example, the triple-helical protein is a collagen protein although it may be any triple-helical protein. The recombinant triple-helical sequence may be derived from any triple-helical or triple-helical containing protein from any source, e.g., prokaryote, bacteria, yeast, spore, plant, insect or silkworm and may be hydroxylated or non-hydroxylated.

Collagen is a major component of the extracellular matrix and it functions to provide tensile strength to tissues as well as influence cell behavior through interactions with cellular receptors. Collagens are ubiquitous in nature. The common feature of the collagen module is a triple-helical structure consisting of three polyproline-II-like helices supercoiled in a right-handed direction around a central axis. The tight packing of the polypeptide chains requires a glycine every third residue, defining the Gly-X-Y repeat motif, where proline and hydroxyproline often occupy the X and Y positions of human collagen respectively. Collagen has been used as a biomaterial in medical, pharmaceutical and consumer products for more than one hundred years. Collagen biomaterials approved for use in humans are predominantly derived from animal sources and have certain limits. These limitations can be overcome by advances in collagen-cell interactions and recombinant protein expression technologies. Collagens as biomaterials have the potential to improve collagen's use in current markets and also Collagens may be used in markets where collagen is not considered an optimal biomaterial. Collagens are highly purified, fully characterized, and can be genetically customized to exhibit desired features for particular applications of interest including presentation of receptor binding motifs. There has been 18,874 collagen-like proteins (CLPs) annotated in bacteria, 695 in viruses, and 157 in archaea. At least 27 genetically different collagen types have been identified, each containing at least one dominant collagenous domain. These collagenous domains have a characteristic triple helix structure formed by repeating Glycine and proline sequences in each participating chain. The collagen monomers often assemble into more complex structures of varying organizations such as fibrils (types I-III, V and XI), networks (types IV, VIII and X) and beaded filaments (type VI). The fibrillar collagen types I and III are the major structural components of the extracellular matrix of skin, cardiac and vascular tissues, whereas type II collagen is a major structural component of cartilage.

The streptococcal collagen-like proteinsin S. pyogenes was designated as Scl and occur in numerous bacterial species. All Scl proteins share a distinct set of conserved features and a similar domain organization. They contain a signal peptide, an N-terminal non-collagenous sequence-variable (V) domain, a central collagen-like (CL) domain, and a cell-wall associated domain containing the LPXTG (SEQ ID NO:29) anchor motif (Gram-positive anchor). The CL domains of different Scl proteins are comprised of varying types of Gly-X-Y triplet repeats, and exhibit significant length variation due to the expansion and contraction of these repeats.

The Scl1 and Scl2 proteins (also known as SclA and SclB) of S. pyogenes are homotrimeric and contain the globular V domain projected away from the cell surface by the rod-shaped CL domain. The V-region sequences differ significantly both between and within Scl1 and Scl2 variants; however, Scl variants are conserved in strains of the same M-type. The Scl1 and Scl2 proteins form stable triple-helical structures. The non-collagenous V region constitutes a trimerization domain that augments proper collagen assembly to avoid the misfolding of the triple helix due to its repeating structure. However, the V domain of Scls is not necessary for triple helix formation in vivo, since the CL region of Scl1 can be expressed in *E. coli* without the V region as recombinant protein in a folded triple-helical state. Scl1 selectively binds cellular, but not plasma, fibronectin and laminin. Both main forms of fibronectin are encoded by a single gene and contain a conserved structure, consisting of three regions of repeats, type I, II, and III. Scl1 proteins specifically bind cFn via recognition of the type III repeat, EDA. EDA/cFn isoforms are found in low levels in normal adult tissue but are upregulated in wounded tissue, where the EDA domain interacts with keratinocyte integrin receptors and is important in the wound healing processes. *S. pyogenes* strains may express multiple fibronectin-binding proteins, including SfbI/PrtF1, PrtF2, SOF, FbaB, SfbX, and Shr that bind the type I and type II repeats; thus, Scl1 binds cFn via unique mechanism different from other Fn-binding proteins of *S. pyogenes*. The putative fibronectin-binding Scl6 proteins of *S. equi* and *S. zooepidemicus*, including FneC, E, and F, likely contribute to colonization of animal hosts. These three proteins contain N-terminal regions similar to the fibronectin-binding domains of the proteins FNE and FNEB of *S. equi*, previously shown to bind fibronectin from horse serum. Interestingly, FNE and FNEB lack the collagen-like domain found in FneC, E, and F. It is possible the Scl6 proteins diverged from FNE/FNEB and acquired the collagenous domain for stability or to project the N-terminal ligand-binding domains in a favorable position for ligand interaction. Therefore, proteins FneC, E, and F that clustered together with the SclZ.6, 9, and 10 proteins are all predicted fibronectin-binding Scl6 proteins. Scls have also been shown to interact with low density lipoprotein and thrombin-activatable fibrinolysis inhibitor. The Scl1.41 variant, expressed by M41-type strains, directly binds human collagen receptors $\alpha_2\beta_1$ and $\alpha_{11}\beta_1$ integrins through the GLPGER (SEQ ID NO:18) motif in the Scl1-collagenous domain. A similar binding motif GF/LOGER (SEQ ID NO:33) (0 represents hydroxyproline), as well as derived sequence motifs GR/AOGER (SEQ ID NO:34) and GASGER (SEQ ID NO:30), were identified in human collagens as integrin-binding sites. In addition, the GAPGER (SEQ ID NO:31) and GKPGER (SEQ ID NO:32) motifs are found in SclZ/Scl3 proteins. The integrin binding motifs RGD and KGD that are found within the collagen triple helix, become active for binding during tissue remodeling. These integrin binding sites are also found in Scl2 and Scl3 proteins.

In addition, the triple helix proteins of the present invention may include integrin binding sites in some embodiments but not in other embodiments. Collagen binding by the four integrins is mediated by a ~200 amino acids long so-called inserted domain (I domain) found between blades 2 and 3 of the β-propeller domain of the α chains. All four I domains ($\alpha_1 I$, $\alpha_2 I$, $\alpha_{10} I$, $\alpha_{11} I$) contain a metal ion-dependent adhesion site (MIDAS) that is required for coordinating a divalent cation and is essential for collagen binding. The integrins are a family of heterodimeric cell surface receptors involved in cell-cell and cell-substrate adhesion. They act as bridging molecules that link intracellular signaling molecules to the extracellular matrix through bi-directional signaling and control cell behavior and tissue architecture. Four integrins, $\alpha 1\beta 1$, $\alpha 2\beta 1$, $\alpha 10\beta 1$ and $\alpha 11\beta 1$ have been shown to bind collagens. Collagen integrin interactions play a role in normal and pathological physiology and directly affect cell adhesion, migration, proliferation and differentiation as well as angiogenesis, platelet aggregation and extracellular matrix assembly.

Thus, in one embodiment of the present invention, there is provided a recombinant synthetic triple helix produced in a prokaryotic expression system. In one preferred form, the recombinant synthetic collagen has a triple helical backbone derived from a Streptococcal protein. Examples include proteins: DC1, DC2, DC3, DC2-3x, DC2-FN.

In addition, the triple helix may have alternative functional sites such as, matrix metalloproteinase (MMP) binding or cleavage sites, discoidin domain-containing receptor (DDR) binding sites, Fibronectin binding sites, bone sialoprotein binding sites, fibrinogen, heparin, decorin binding sites, fibromodulin binding sites, lumican binding sites, or other binding sites.

Functional sites may be added to the triple helical protein to facilitate purification of such triple helical protein, enzymatic cleavage sites, or changes that results in stabilizing the triple helix such as with cysteines or fold-on motifs or with residues that increase the melting temperature. In order to prevent adhesions, the triple helical protein may be formulated to comprise a spray, gel, a sheet and may be combined with polymers, or other ECM materials to achieve appropriate tensile strength or architecture. In addition the composition may be applied internally in any cavity or region in any animal including animal is a human, a dog, a cat, a mouse, a rat, a monkey, a goat, a pig, a cow, a hamster, a rabbit, a horse, a sheep, a guinea pig, or a bird.

Furthermore the protein, the motif or both may be isolated for any source bacteria, viruses, archaea, etc. (e.g., streptococcal collagen-like proteins, Scl, in *S. pyogenes*, *Bacillus* proteins Bcl, pneumococcal protein Pcl, Lcl of *Legionella pneumophila*, and Bud proteins of *Burkholderia* spp.

The present invention may include the DC1 sequence, DC1 collagen domain sequence, DC2 sequence, DC2 collagen domain sequence, ecollagen sequence, ecollagen collagen domain sequence; DC2-3x sequence, DC2-3x collagen domain sequence, DC2-FN sequence, DC2-FN collagen domain sequence, DC2-Thrombin sequence, DC2-Thrombin collagen domain sequence, DC2-Pepsin sequence, DC2-Pepsin collagen domain sequence, DC1-DDR1 sequence, DC1-DDR1 collagen domain sequence or a combination thereof in one or multiple repeats.

FIGS. 1A-1O shows the amino acid sequences of constructs used to block adhesion of the present invention. FIG. 1A shows the DC1 sequence (SEQ ID NO:1). FIG. 1B shows the DC1 collagen domain sequence (SEQ ID NO:2). FIG. 1C shows the DC2 sequence (SEQ ID NO:3). FIG. 1D shows the DC2 collagen domain sequence (SEQ ID NO:4). FIG. 1E shows the ecollagen sequence (SEQ ID NO:5). FIG. 1F shows the ecollagen collagen domain sequence (SEQ ID NO:6). FIG. 1G shows the DC2-3x sequence (SEQ ID NO:7). FIG. 1H shows the DC2-3x collagen domain sequence (SEQ ID NO:8). FIG. 1I shows the DC2-FN sequence (SEQ ID NO:9). FIG. 1J shows the DC2-FN collagen domain sequence (SEQ ID NO:10). FIG. 1K shows the DC2-Thrombin sequence (SEQ ID NO:11). FIG. 1L shows the DC2-Thrombin collagen domain sequence (SEQ ID NO:12). FIG. 1M shows the DC2-Pepsin sequence (SEQ ID NO:13). FIG. 1N shows the DC2-Pepsin collagen domain sequence (SEQ ID NO:14). FIG. 1O shows the DC1-DDR1 sequence (SEQ ID NO:15). FIG. 1P shows the DC1-DDR1 collagen domain sequence (SEQ ID NO:16).

The triple helix anti-adhesion proteins of the present invention were tested to demonstrate the anti-adhesion properties. The triple helix anti-adhesion protein DC1, DC2, DC3, DC2-3x, DC2-FN, Type 1 Collagen, and PBS. The anti-adhesion properties were tested on 42 Sprague Dawley rats. They were all female (requested 20 male and 22 female) and weighed ~250 g. FIGS. 2 and 3 are images of the surgery. Surgery was performed on and the animals were anesthetized with isoflurane in oxygen and maintained on isoflurane in oxygen via a nose cone. The ventral abdomen was clipped and prepped for surgery with chlorohexidine and 70% ethanol. The abdomen was draped with a paper drape and a 2 cm ventral mid-line incision made in the central ⅓ of the abdomen. The cecum was exteriorized and a template used to abrade the cecal serosa in a standard location, size, and severity of abrasion (40 strokes of a dry gauze with mild pressure). Similarly, a 1 cm×1 cm area of body wall was resected from the right side of the abdomen centered 1 cm dorsal to the incision. A single simple interrupted suture (5-0 monocryl) was placed between the cecum and the body wall at a site ~1 cm distant to the abraded area of both the cecum and body wall in order to hold those 2 damaged areas in close proximity to mimic the post-operative ileus suggested to be a contributing factor to adhesion formation (see image below). The treatments were then applied (1.5 ml total) making every effort to coat the abraded surfaces with the treatment. The treatment was performed in a blind study. The body wall was closed with 5-0 PDS in a simple continuous pattern and the skin was closed with 5-0 PDS in a simple continuous pattern. All animals were administered buprenorphine (0.01 mg/ml subq) immediately post-operatively. Treatments involved 7 treatment groups with 6 animals in each group. Each of the treatment groups received a different triple helix protein 1. DC1; 2. DC2; 3. DC3; 4. DC2-3x; 5. DC2-FN; 6. Type 1 Collagen; and 7. PBS. In the immediate post-operative period several animals chewed on their incisions. Several required repair and 3 animals were euthanized given the damage to their incision. These incisions were not closed differently than previous iterations of this project and this is the first occurrence of this complication. Discussions with LARR veterinarians revealed that this is an inherent risk of abdominal surgery of rats that sometimes occurs. In future tissue adhesive will also be used to limit the rats' ability to chew out sutures. After the first 24 hours there were no additional incisional problems and all of the remaining rats appeared normal. Adhesion Scoring: All animals were euthanized via $CO_2$ asphyxiation. The abdominal wall was opened at the left flank (to avoid disturbing site of adhesion) and retracted to expose the right body wall. Any adhesions were photographed and adhesions scored as previously described (Table 1 below). One observer blinded to treatment group scored all of the animals. The area of adhesion and ~2 mm of surrounding cecal wall and body wall were resected and formalin fixed.

TABLE 1

| | Area Score |
|---|---|
| 0 | No Adhesion |
| 1 | Cecum to bowel adhesion |
| 2 | Cecum to body wall (<25% of abraded area) |
| 3 | Cecum to body wall (25%-50% of abraded area) |
| 4 | Cecum to body wall (50-100% of abraded area) |
| 5 | Cecum to body wall (>100% of abraded area) |
| | Strength Score |
| 0 | No Adhesion |
| 1 | Gentle Traction required to break adhesion |

TABLE 1-continued

| 2 | Blunt Dissection required to break adhesion |
|---|---|
| 3 | Sharp dissection required to break adhesion |
| | Gross Adhesion Maturity Score |
| 0 | No Adhesion |
| 1 | Filmy Adhesion |
| 2 | Vascularized adhesion |
| 3 | Opaque or cohesive adhesion |

In addition to the scores above a "composite" score was calculated in an attempt to capture the differences between adhesions as the small scale of the scoring system (i.e. 1-3) does not allow for much difference between very large, mature adhesions and smaller, less cohesive adhesions. The composite score was calculated as below:

Composite score=size×(strength+maturity)

FIGS. 4A-4E are scatter plots with mean and 95% confidence interval (CI) of each of the variables shown. From the plots in FIGS. 4A-4E the means of DC1, DC2, and DC3 are encouraging, there remains a substantial amount of variability with these groups. DC2-3X, DC2-FN, CT-1, and PBS were more uniform with consistent large, mature adhesions.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The present application incorporates by reference U.S. patent application Ser. No. 14/095,451; U.S. patent application Ser. No. 12/804,306; U.S. Provisional Application No. 61/335,432; and U.S. Provisional Application No. 61/271,218.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of reducing or eliminating tissue adhesion or fibrosis comprising the steps of:
   providing a non-thrombogenic collagen fusion protein comprising the sequence of SEQ ID NO: 7 that facilitates reducing or eliminating tissue adhesion or fibrosis in a biocompatible carrier, and
   applying the non-thrombogenic collagen fusion protein comprising the sequence of SEQ ID NO: 7 in a biocompatible carrier to a damaged area for reducing or eliminating tissue adhesion or fibrosis.

2. The method of claim 1, wherein the damaged area in need of reducing or eliminating adhesion is an incision.

3. The method of claim 1, wherein the biocompatible carrier comprises a spray, a foam, a solution, a gel, a sheet, a strip, a tube, a liquid, a paste, a wax or other material.

4. The method of claim 1, wherein the biocompatible carrier comprises one or more polymers or other extracellular matrix (ECM) materials to achieve appropriate tensile strength or architecture desired.

5. The method of claim 1, wherein the damaged area is an open surgery, minimally invasive surgery, hernia surgery, open-heart surgery, surgery of a ligament, surgery of a meniscus, surgery of a patella, mouth sores, oral lesions, tissue bone regeneration, periodontal regeneration, oral reconstruction, vestibuloplasty, tissue regeneration around dental implants, esophagus reconstruction, plastic surgery, cosmetic surgery, peripheral arterial disease, ladder reconstruction, orbital floor repair, ulcers, corneal repair, spinal implant, general surgery, vascular conduits, gingival, genitourinary reconstruction, celioscopy, nasoscopy, laryngoscopy, endoscopy, peritoneal cavity in peritoneal dialysis or laparoscopy.

6. The method of claim 1, wherein the fibrosis is from a fibrosing disease, scleroderma, pulmonary fibrosis, asthma, keloid scarring, rheumatoid arthritis, lupus, nephrogenic fibrosing dermopathy, fibrotic lesions formed after *Schistosoma japonicum* infection, autoimmune diseases, Lyme disease, stromal remodeling in pancreatitis and stromal fibrosis, chronic obstructive pulmonary disease, uterine fibroids, ovarian fibrosis, other fibrocystic formations, corneal fibrosis or other eye fibrosis, such as that resulting from corneal refraction surgery, fibrosis resulting from congestive heart failure and other post-ischemic conditions, abdominal adhesions, wide angle glaucoma trabeculotomy, endometriosis, and any combinations thereof.

\* \* \* \* \*

```
                        SEQUENCE LISTING

<160> NUMBER OF SEQ ID NOS: 26

<210> SEQ ID NO 1
<211> LENGTH: 339
<212> TYPE: PRT
<213> ORGANISM: Artificial Sequence
<220> FEATURE:
<223> OTHER INFORMATION: Synthetic peptide

<400> SEQUENCE: 1

Met Asn His Lys Val His His His His His Met Glu Leu Asp Glu
1               5                   10                  15

Gln Glu Glu Lys Ala Lys Val Arg Thr Glu Leu Ile Gln Glu Leu Ala
                20                  25                  30

Gln Gly Leu Gly Gly Ile Glu Lys Lys Asn Phe Pro Thr Leu Gly Asp
                35                  40                  45

Glu Asp Leu Asp His Thr Tyr Met Thr Lys Leu Leu Thr Tyr Leu Gln
        50                  55                  60

Glu Arg Glu Gln Ala Glu Asn Ser Trp Arg Lys Arg Leu Leu Lys Gly
65                  70                  75                  80

Ile Gln Asp His Ala Leu Asp Gly Gln Asp Gly Arg Asn Gly Glu Arg
                85                  90                  95

Gly Glu Gln Gly Pro Thr Gly Pro Thr Gly Pro Ala Gly Pro Arg Gly
                100                 105                 110

Leu Gln Gly Leu Gln Gly Leu Gln Gly Glu Arg Gly Glu Gln Gly Pro
        115                 120                 125

Thr Gly Pro Ala Gly Pro Arg Gly Leu Gln Gly Glu Arg Gly Glu Gln
        130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Pro Arg Gly Glu Gln Gly Pro
                165                 170                 175

Gln Gly Leu Pro Gly Lys Asp Gly Glu Ala Gly Ala Gln Gly Pro Ala
                180                 185                 190

Gly Pro Met Gly Pro Ala Gly Glu Arg Gly Glu Lys Gly Glu Pro Gly
        195                 200                 205

Thr Gln Gly Ala Lys Gly Asp Arg Gly Glu Thr Gly Pro Val Gly Pro
        210                 215                 220

Arg Gly Glu Arg Gly Glu Ala Gly Pro Ala Gly Lys Asp Gly Glu Arg
225                 230                 235                 240

Gly Pro Val Gly Pro Ala Gly Lys Asp Gly Gln Asn Gly Gln Asp Gly
```

```
                    245                 250                 255

Leu Pro Gly Lys Asp Gly Lys Asp Gly Gln Asn Gly Lys Asp Gly Leu
            260                 265                 270

Pro Gly Lys Asp Gly Lys Asp Gly Gln Asn Gly Lys Asp Gly Leu Pro
            275                 280                 285

Gly Lys Asp Gly Lys Asp Gly Gln Asp Gly Lys Asp Gly Leu Pro Gly
            290                 295                 300

Lys Asp Gly Lys Asp Gly Leu Pro Gly Lys Asp Gly Lys Asp Gly Gln
305                 310                 315                 320

Pro Gly Lys Pro Ala Pro Lys Thr Pro Glu Val Pro Gln Lys Pro Asp
            325                 330                 335

Thr Ala Pro

<210> SEQ ID NO 2
<211> LENGTH: 237
<212> TYPE: PRT
<213> ORGANISM: Artificial Sequence
<220> FEATURE:
<223> OTHER INFORMATION: Synthetic peptide

<400> SEQUENCE: 2

Gly Gln Asp Gly Arg Asn Gly Glu Arg Gly Glu Gln Gly Pro Thr Gly
1               5                   10                  15

Pro Thr Gly Pro Ala Gly Pro Arg Gly Leu Gln Gly Leu Gln Gly Leu
            20                  25                  30

Gln Gly Glu Arg Gly Glu Gln Gly Pro Thr Gly Pro Ala Gly Pro Arg
        35                  40                  45

Gly Leu Gln Gly Glu Arg Gly Glu Gln Gly Pro Thr Gly Leu Ala Gly
    50                  55                  60

Lys Ala Gly Glu Ala Gly Ala Lys Gly Glu Thr Gly Pro Ala Gly Pro
65                  70                  75                  80

Gln Gly Pro Arg Gly Glu Gln Gly Pro Gln Gly Leu Pro Gly Lys Asp
            85                  90                  95

Gly Glu Ala Gly Ala Gln Gly Pro Ala Gly Pro Met Gly Pro Ala Gly
            100                 105                 110

Glu Arg Gly Glu Lys Gly Glu Pro Gly Thr Gln Gly Ala Lys Gly Asp
        115                 120                 125

Arg Gly Glu Thr Gly Pro Val Gly Pro Arg Gly Glu Arg Gly Glu Ala
    130                 135                 140

Gly Pro Ala Gly Lys Asp Gly Glu Arg Gly Pro Val Gly Pro Ala Gly
145                 150                 155                 160

Lys Asp Gly Gln Asn Gly Gln Asp Gly Leu Pro Gly Lys Asp Gly Lys
            165                 170                 175

Asp Gly Gln Asn Gly Lys Asp Gly Leu Pro Gly Lys Asp Gly Lys Asp
            180                 185                 190

Gly Gln Asn Gly Lys Asp Gly Leu Pro Gly Lys Asp Gly Lys Asp Gly
        195                 200                 205

Gln Asp Gly Lys Asp Gly Leu Pro Gly Lys Asp Gly Lys Asp Gly Leu
    210                 215                 220

Pro Gly Lys Asp Gly Lys Asp Gly Gln Pro Gly Lys Pro
225                 230                 235

<210> SEQ ID NO 3
<211> LENGTH: 339
<212> TYPE: PRT
<213> ORGANISM: Artificial Sequence
```

<220> FEATURE:
<223> OTHER INFORMATION: Synthetic peptide

<400> SEQUENCE: 3

```
Met Asn His Lys Val His His His His His Met Glu Leu Asp Glu
1               5                   10                  15

Gln Glu Glu Lys Ala Lys Val Arg Thr Glu Leu Ile Gln Glu Leu Ala
            20                  25                  30

Gln Gly Leu Gly Gly Ile Glu Lys Lys Asn Phe Pro Thr Leu Gly Asp
            35                  40                  45

Glu Asp Leu Asp His Thr Tyr Met Thr Lys Leu Leu Thr Tyr Leu Gln
        50                  55                  60

Glu Arg Glu Gln Ala Glu Asn Ser Trp Arg Lys Arg Leu Leu Lys Gly
65                  70                  75                  80

Ile Gln Asp His Ala Leu Asp Gly Gln Asp Gly Arg Asn Gly Glu Arg
                85                  90                  95

Gly Glu Gln Gly Pro Thr Gly Pro Thr Gly Pro Ala Gly Pro Arg Gly
            100                 105                 110

Leu Gln Gly Leu Gln Gly Phe Pro Gly Glu Arg Gly Glu Gln Gly Pro
        115                 120                 125

Thr Gly Pro Ala Gly Pro Arg Gly Leu Gln Gly Glu Arg Gly Glu Gln
    130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Arg Gly Glu Gln Gly Pro
                165                 170                 175

Gln Gly Leu Pro Gly Lys Asp Gly Glu Ala Gly Ala Gln Gly Pro Ala
            180                 185                 190

Gly Pro Met Gly Pro Ala Gly Glu Arg Gly Glu Lys Gly Glu Pro Gly
            195                 200                 205

Thr Gln Gly Ala Lys Gly Asp Arg Gly Glu Thr Gly Pro Val Gly Pro
    210                 215                 220

Arg Gly Glu Arg Gly Glu Ala Gly Pro Ala Gly Lys Asp Gly Glu Arg
225                 230                 235                 240

Gly Pro Val Gly Pro Ala Gly Lys Asp Gly Gln Asn Gly Gln Asp Gly
            245                 250                 255

Leu Pro Gly Lys Asp Gly Lys Asp Gly Gln Asn Gly Lys Asp Gly Leu
            260                 265                 270

Pro Gly Lys Asp Gly Lys Asp Gly Gln Asn Gly Lys Asp Gly Leu Pro
        275                 280                 285

Gly Lys Asp Gly Lys Asp Gly Gln Asp Gly Lys Asp Gly Leu Pro Gly
    290                 295                 300

Lys Asp Gly Lys Asp Gly Leu Pro Gly Lys Asp Gly Lys Asp Gly Gln
305                 310                 315                 320

Pro Gly Lys Pro Ala Pro Lys Thr Pro Glu Val Pro Gln Lys Pro Asp
            325                 330                 335

Thr Ala Pro
```

<210> SEQ ID NO 4
<211> LENGTH: 237
<212> TYPE: PRT
<213> ORGANISM: Artificial Sequence
<220> FEATURE:
<223> OTHER INFORMATION: Synthetic peptide

<400> SEQUENCE: 4

```
Gly Gln Asp Gly Arg Asn Gly Glu Arg Gly Glu Gln Gly Pro Thr Gly
1               5                   10                  15

Pro Thr Gly Pro Ala Gly Pro Arg Gly Leu Gln Gly Leu Gln Gly Phe
            20                  25                  30

Pro Gly Glu Arg Gly Glu Gln Gly Pro Thr Gly Pro Ala Gly Pro Arg
            35                  40                  45

Gly Leu Gln Gly Glu Arg Gly Glu Gln Gly Pro Thr Gly Leu Ala Gly
        50                  55                  60

Lys Ala Gly Glu Ala Gly Ala Lys Gly Glu Thr Gly Pro Ala Gly Pro
65                  70                  75                  80

Gln Gly Pro Arg Gly Glu Gln Gly Pro Gln Gly Leu Pro Gly Lys Asp
            85                  90                  95

Gly Glu Ala Gly Ala Gln Gly Pro Ala Gly Pro Met Gly Pro Ala Gly
            100                 105                 110

Glu Arg Gly Glu Lys Gly Glu Pro Gly Thr Gln Gly Ala Lys Gly Asp
            115                 120                 125

Arg Gly Glu Thr Gly Pro Val Gly Pro Arg Gly Glu Arg Gly Glu Ala
            130                 135                 140

Gly Pro Ala Gly Lys Asp Gly Glu Arg Gly Pro Val Gly Pro Ala Gly
145                 150                 155                 160

Lys Asp Gly Gln Asn Gly Gln Asp Gly Leu Pro Gly Lys Asp Gly Lys
            165                 170                 175

Asp Gly Gln Asn Gly Lys Asp Gly Leu Pro Gly Lys Asp Gly Lys Asp
            180                 185                 190

Gly Gln Asn Gly Lys Asp Gly Leu Pro Gly Lys Asp Gly Lys Asp Gly
            195                 200                 205

Gln Asp Gly Lys Asp Gly Leu Pro Gly Lys Asp Gly Lys Asp Gly Leu
            210                 215                 220

Pro Gly Lys Asp Gly Lys Asp Gly Gln Pro Gly Lys Pro
225                 230                 235
```

<210> SEQ ID NO 5
<211> LENGTH: 339
<212> TYPE: PRT
<213> ORGANISM: Artificial Sequence
<220> FEATURE:
<223> OTHER INFORMATION: Synthetic peptide

<400> SEQUENCE: 5

```
Met Asn His Lys Val His His His His His Met Glu Leu Asp Glu
1               5                   10                  15

Gln Glu Glu Lys Ala Lys Val Arg Thr Glu Leu Ile Gln Glu Leu Ala
            20                  25                  30

Gln Gly Leu Gly Gly Ile Glu Lys Lys Asn Phe Pro Thr Leu Gly Asp
            35                  40                  45

Glu Asp Leu Asp His Thr Tyr Met Thr Lys Leu Leu Thr Tyr Leu Gln
        50                  55                  60

Glu Arg Glu Gln Ala Glu Asn Ser Trp Arg Lys Arg Leu Leu Lys Gly
65                  70                  75                  80

Ile Gln Asp His Ala Leu Asp Gly Gln Asp Gly Arg Asn Gly Glu Arg
            85                  90                  95

Gly Glu Gln Gly Pro Thr Gly Pro Thr Gly Pro Ala Gly Pro Arg Gly
            100                 105                 110

Leu Gln Gly Leu Gln Gly Phe Pro Gly Glu Arg Gly Glu Gln Gly Pro
            115                 120                 125
```

Thr Gly Pro Ala Gly Pro Arg Gly Leu Gln Gly Glu Arg Gly Glu Gln
            130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Pro Arg Gly Glu Gln Gly Pro
                165                 170                 175

Gln Gly Leu Pro Gly Arg Asp Gly Glu Ala Gly Ala Gln Gly Pro Ala
            180                 185                 190

Gly Pro Met Gly Pro Ala Gly Glu Arg Gly Glu Lys Gly Glu Pro Gly
        195                 200                 205

Thr Gln Gly Ala Lys Gly Asp Arg Gly Glu Thr Gly Pro Val Gly Pro
210                 215                 220

Arg Gly Glu Arg Gly Glu Ala Gly Pro Ala Gly Arg Asp Gly Glu Arg
225                 230                 235                 240

Gly Pro Val Gly Pro Ala Gly Arg Asp Gly Gln Asn Gly Gln Asp Gly
                245                 250                 255

Leu Pro Gly Lys Asp Gly Arg Asp Gly Gln Asn Gly Arg Asp Gly Leu
            260                 265                 270

Pro Gly Arg Asp Gly Arg Asp Gly Gln Asn Gly Arg Asp Gly Leu Pro
        275                 280                 285

Gly Arg Asp Gly Arg Asp Gly Gln Asp Gly Arg Asp Gly Leu Pro Gly
290                 295                 300

Arg Asp Gly Arg Asp Gly Leu Pro Gly Asp Arg Gly Glu Arg Gly Gln
305                 310                 315                 320

Pro Gly Arg Pro Ala Pro Lys Thr Pro Glu Val Pro Gln Lys Pro Asp
                325                 330                 335

Thr Ala Pro

<210> SEQ ID NO 6
<211> LENGTH: 237
<212> TYPE: PRT
<213> ORGANISM: Artificial Sequence
<220> FEATURE:
<223> OTHER INFORMATION: Synthetic peptide

<400> SEQUENCE: 6

Gly Gln Asp Gly Arg Asn Gly Glu Arg Gly Gln Gly Pro Thr Gly
1               5                   10                  15

Pro Thr Gly Pro Ala Gly Pro Arg Gly Leu Gln Gly Leu Gln Gly Phe
                20                  25                  30

Pro Gly Glu Arg Gly Glu Gln Gly Pro Thr Gly Pro Ala Gly Pro Arg
            35                  40                  45

Gly Leu Gln Gly Glu Arg Gly Glu Gln Gly Pro Thr Gly Leu Ala Gly
        50                  55                  60

Lys Ala Gly Glu Ala Gly Ala Lys Gly Glu Thr Gly Pro Ala Gly Pro
65                  70                  75                  80

Gln Gly Pro Arg Gly Glu Gln Gly Pro Gln Gly Leu Pro Gly Arg Asp
                85                  90                  95

Gly Glu Ala Gly Ala Gln Gly Pro Ala Gly Met Gly Pro Ala Gly
            100                 105                 110

Glu Arg Gly Glu Lys Gly Glu Pro Gly Thr Gln Gly Ala Lys Gly Asp
        115                 120                 125

Arg Gly Glu Thr Gly Pro Val Gly Pro Arg Gly Glu Arg Gly Glu Ala
    130                 135                 140

Gly Pro Ala Gly Arg Asp Gly Glu Arg Gly Pro Val Gly Pro Ala Gly
145                 150                 155                 160

Arg Asp Gly Gln Asn Gly Gln Asp Gly Leu Pro Gly Lys Asp Gly Arg
            165                 170                 175

Asp Gly Gln Asn Gly Arg Asp Gly Leu Pro Gly Arg Asp Gly Arg Asp
        180                 185                 190

Gly Gln Asn Gly Arg Asp Gly Leu Pro Gly Arg Asp Gly Arg Asp Gly
    195                 200                 205

Gln Asp Gly Arg Asp Gly Leu Pro Gly Arg Asp Gly Arg Asp Gly Leu
    210                 215                 220

Pro Gly Asp Arg Gly Glu Arg Gly Gln Pro Gly Arg Pro
225                 230                 235

<210> SEQ ID NO 7
<211> LENGTH: 339
<212> TYPE: PRT
<213> ORGANISM: Artificial Sequence
<220> FEATURE:
<223> OTHER INFORMATION: Synthetic peptide

<400> SEQUENCE: 7

Met Asn His Lys Val His His His His His Met Glu Leu Asp Glu
1               5                   10                  15

Gln Glu Glu Lys Ala Lys Val Arg Thr Glu Leu Ile Gln Glu Leu Ala
            20                  25                  30

Gln Gly Leu Gly Gly Ile Glu Lys Lys Asn Phe Pro Thr Leu Gly Asp
        35                  40                  45

Glu Asp Leu Asp His Thr Tyr Met Thr Lys Leu Leu Thr Tyr Leu Gln
    50                  55                  60

Glu Arg Glu Gln Ala Glu Asn Ser Trp Arg Lys Arg Leu Leu Lys Gly
65                  70                  75                  80

Ile Gln Asp His Ala Leu Asp Gly Gln Asp Gly Arg Asn Gly Glu Arg
                85                  90                  95

Gly Glu Gln Gly Pro Thr Gly Pro Thr Gly Pro Ala Gly Pro Arg Gly
            100                 105                 110

Leu Gln Gly Leu Gln Gly Phe Pro Gly Glu Arg Gly Glu Gln Gly Pro
        115                 120                 125

Thr Gly Pro Ala Gly Pro Arg Gly Leu Gln Gly Glu Arg Gly Glu Gln
    130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Pro Arg Gly Glu Gln Gly Pro
                165                 170                 175

Gln Gly Leu Pro Gly Phe Pro Gly Glu Arg Gly Ala Gln Gly Pro Ala
            180                 185                 190

Gly Pro Met Gly Pro Ala Gly Glu Arg Gly Lys Gly Glu Pro Gly
        195                 200                 205

Thr Gln Gly Ala Lys Gly Asp Arg Gly Glu Thr Gly Pro Val Gly Pro
    210                 215                 220

Arg Gly Glu Arg Gly Glu Ala Gly Pro Ala Gly Lys Asp Gly Glu Arg
225                 230                 235                 240

Gly Pro Val Gly Pro Ala Gly Lys Asp Gly Gln Asn Gly Gln Asp Gly
                245                 250                 255

Phe Pro Gly Lys Asp Gly Lys Asp Gly Gln Asn Gly Lys Asp Gly Leu
            260                 265                 270

```
Pro Gly Lys Asp Gly Lys Asp Gly Gln Asn Gly Lys Asp Gly Leu Pro
            275                 280                 285

Gly Lys Asp Gly Lys Asp Gly Gln Asp Gly Lys Asp Gly Leu Pro Gly
        290                 295                 300

Lys Asp Gly Lys Asp Gly Phe Pro Gly Glu Arg Gly Lys Asp Gly Gln
305                 310                 315                 320

Pro Gly Lys Pro Ala Pro Lys Thr Pro Glu Val Pro Gln Lys Pro Asp
            325                 330                 335

Thr Ala Pro

<210> SEQ ID NO 8
<211> LENGTH: 237
<212> TYPE: PRT
<213> ORGANISM: Artificial Sequence
<220> FEATURE:
<223> OTHER INFORMATION: Synthetic peptide

<400> SEQUENCE: 8

Gly Gln Asp Gly Arg Asn Gly Glu Arg Gly Gln Gly Pro Thr Gly
1               5                   10                  15

Pro Thr Gly Pro Ala Gly Pro Arg Gly Leu Gln Gly Leu Gln Gly Phe
            20                  25                  30

Pro Gly Glu Arg Gly Glu Gln Gly Pro Thr Gly Pro Ala Gly Pro Arg
        35                  40                  45

Gly Leu Gln Gly Glu Arg Gly Glu Gln Gly Pro Thr Gly Leu Ala Gly
    50                  55                  60

Lys Ala Gly Glu Ala Gly Ala Lys Gly Glu Thr Gly Pro Ala Gly Pro
65                  70                  75                  80

Gln Gly Pro Arg Gly Glu Gln Gly Pro Gln Gly Leu Pro Gly Phe Pro
                85                  90                  95

Gly Glu Arg Gly Ala Gln Gly Pro Ala Gly Pro Met Gly Pro Ala Gly
            100                 105                 110

Glu Arg Gly Glu Lys Gly Glu Pro Gly Thr Gln Gly Ala Lys Gly Asp
        115                 120                 125

Arg Gly Glu Thr Gly Pro Val Gly Pro Arg Gly Glu Arg Gly Glu Ala
    130                 135                 140

Gly Pro Ala Gly Lys Asp Gly Glu Arg Gly Pro Val Gly Pro Ala Gly
145                 150                 155                 160

Lys Asp Gly Gln Asn Gly Gln Asp Gly Phe Pro Gly Lys Asp Gly Lys
                165                 170                 175

Asp Gly Gln Asn Gly Lys Asp Gly Leu Pro Gly Lys Asp Gly Lys Asp
            180                 185                 190

Gly Gln Asn Gly Lys Asp Gly Leu Pro Gly Lys Asp Gly Lys Asp Gly
        195                 200                 205

Gln Asp Gly Lys Asp Gly Leu Pro Gly Lys Asp Gly Lys Asp Gly Phe
    210                 215                 220

Pro Gly Glu Arg Gly Lys Asp Gly Gln Pro Gly Lys Pro
225                 230                 235

<210> SEQ ID NO 9
<211> LENGTH: 348
<212> TYPE: PRT
<213> ORGANISM: Artificial Sequence
<220> FEATURE:
<223> OTHER INFORMATION: Synthetic peptide

<400> SEQUENCE: 9
```

```
Met Asn His Lys Val His His His His His Met Glu Leu Asp Glu
1               5                   10                  15

Gln Glu Glu Lys Ala Lys Val Arg Thr Glu Leu Ile Gln Glu Leu Ala
            20                  25                  30

Gln Gly Leu Gly Gly Ile Glu Lys Lys Asn Phe Pro Thr Leu Gly Asp
            35                  40                  45

Glu Asp Leu Asp His Thr Tyr Met Thr Lys Leu Leu Thr Tyr Leu Gln
 50              55                  60

Glu Arg Glu Gln Ala Glu Asn Ser Trp Arg Lys Arg Leu Leu Lys Gly
 65              70                  75                  80

Ile Gln Asp His Ala Leu Asp Gly Gln Asp Gly Arg Asn Gly Glu Arg
                85                  90                  95

Gly Glu Gln Gly Pro Thr Gly Pro Thr Gly Ala Gly Pro Arg Gly
                100             105                 110

Leu Gln Gly Leu Gln Gly Phe Pro Gly Glu Arg Gly Glu Gln Gly Pro
            115                 120                 125

Thr Gly Pro Ala Gly Pro Arg Gly Leu Gln Gly Glu Arg Gly Glu Gln
            130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Pro Arg Gly Glu Gln Gly Pro
                165                 170                 175

Gln Gly Leu Pro Gly Lys Asp Gly Glu Ala Gly Ala Gln Gly Pro Ala
            180                 185                 190

Gly Pro Met Gly Pro Ala Gly Glu Arg Gly Lys Gly Glu Pro Gly
            195                 200                 205

Thr Gln Gly Ala Lys Gly Asp Arg Gly Glu Thr Gly Pro Val Gly Pro
 210                215                 220

Arg Gly Glu Arg Gly Glu Ala Gly Pro Ala Gly Lys Asp Gly Glu Arg
225                 230                 235                 240

Gly Pro Val Gly Pro Ala Gly Lys Asp Gly Gln Asn Gly Gln Asp Gly
                245                 250                 255

Leu Pro Gly Lys Asp Gly Lys Asp Gly Gln Asn Gly Lys Asp Gly Leu
            260                 265                 270

Pro Gly Lys Asp Gly Lys Asp Gly Gln Asn Gly Lys Asp Gly Leu Pro
            275                 280                 285

Gly Lys Asp Gly Lys Asp Gly Gln Asp Gly Lys Asp Gly Leu Pro Gly
            290                 295                 300

Lys Asp Gly Lys Asp Gly Leu Pro Gly Lys Asp Gly Leu Ala Gly Gln
305                 310                 315                 320

Arg Gly Ile Val Gly Leu Pro Gly Gln Arg Gly Glu Arg Ala Pro Lys
                325                 330                 335

Thr Pro Glu Val Pro Gln Lys Pro Asp Thr Ala Pro
                340                 345
```

<210> SEQ ID NO 10
<211> LENGTH: 246
<212> TYPE: PRT
<213> ORGANISM: Artificial Sequence
<220> FEATURE:
<223> OTHER INFORMATION: Synthetic peptide

<400> SEQUENCE: 10

```
Gly Gln Asp Gly Arg Asn Gly Glu Arg Gly Glu Gln Gly Pro Thr Gly
1               5                   10                  15
```

-continued

Pro Thr Gly Pro Ala Gly Pro Arg Gly Leu Gln Gly Leu Gln Gly Phe
            20                  25                  30

Pro Gly Glu Arg Gly Glu Gln Gly Pro Thr Gly Ala Gly Pro Arg
        35                  40                  45

Gly Leu Gln Gly Glu Arg Gly Glu Gln Gly Pro Thr Gly Leu Ala Gly
50                  55                  60

Lys Ala Gly Glu Ala Gly Ala Lys Gly Glu Thr Gly Pro Ala Gly Pro
65                  70                  75                  80

Gln Gly Pro Arg Gly Gln Gly Pro Gly Leu Pro Gly Lys Asp
                85                  90                  95

Gly Glu Ala Gly Ala Gln Gly Pro Ala Gly Pro Met Gly Pro Ala Gly
            100                 105                 110

Glu Arg Gly Glu Lys Gly Glu Pro Gly Thr Gln Gly Ala Lys Gly Asp
        115                 120                 125

Arg Gly Glu Thr Gly Pro Val Gly Pro Arg Gly Glu Arg Gly Glu Ala
        130                 135                 140

Gly Pro Ala Gly Lys Asp Gly Glu Arg Gly Pro Val Gly Pro Ala Gly
145                 150                 155                 160

Lys Asp Gly Gln Asn Gly Gln Asp Gly Leu Pro Gly Lys Asp Gly Lys
                165                 170                 175

Asp Gly Gln Asn Gly Lys Asp Gly Leu Pro Gly Lys Asp Gly Lys Asp
            180                 185                 190

Gly Gln Asn Gly Lys Asp Gly Leu Pro Gly Lys Asp Gly Lys Asp Gly
        195                 200                 205

Gln Asp Gly Lys Asp Gly Leu Pro Gly Lys Asp Gly Lys Asp Gly Leu
210                 215                 220

Pro Gly Lys Asp Gly Leu Ala Gly Gln Arg Gly Ile Val Gly Leu Pro
225                 230                 235                 240

Gly Gln Arg Gly Glu Arg
            245

<210> SEQ ID NO 11
<211> LENGTH: 352
<212> TYPE: PRT
<213> ORGANISM: Artificial Sequence
<220> FEATURE:
<223> OTHER INFORMATION: Synthetic peptide

<400> SEQUENCE: 11

Met Asn His Lys Val His His His His His Met Glu Leu Asp Glu
1               5                   10                  15

Gln Glu Glu Lys Ala Lys Val Arg Thr Glu Leu Ile Gln Glu Leu Ala
            20                  25                  30

Gln Gly Leu Gly Gly Ile Glu Lys Lys Asn Phe Pro Thr Leu Gly Asp
        35                  40                  45

Glu Asp Leu Asp His Thr Tyr Met Thr Lys Leu Leu Thr Tyr Leu Gln
50                  55                  60

Glu Arg Glu Gln Ala Glu Asn Ser Trp Arg Lys Arg Leu Leu Lys Gly
65                  70                  75                  80

Ile Gln Asp His Ala Leu Asp Leu Val Pro Arg Gly Ser Pro Gly Leu
                85                  90                  95

Pro Gly Pro Arg Gly Gln Asp Gly Arg Asn Gly Glu Arg Gly Glu Gln
            100                 105                 110

Gly Pro Thr Gly Pro Thr Gly Pro Ala Gly Pro Arg Gly Leu Gln Gly
        115                 120                 125

-continued

```
Leu Gln Gly Phe Pro Gly Glu Arg Gly Glu Gln Gly Pro Thr Gly Pro
    130                 135                 140

Ala Gly Pro Arg Gly Leu Gln Gly Glu Arg Gly Glu Gln Gly Pro Thr
145                 150                 155                 160

Gly Leu Ala Gly Lys Ala Gly Glu Ala Gly Ala Lys Gly Glu Thr Gly
                165                 170                 175

Pro Ala Gly Pro Gln Gly Pro Arg Gly Glu Gln Gly Pro Gln Gly Leu
            180                 185                 190

Pro Gly Lys Asp Gly Glu Ala Gly Ala Gln Gly Pro Ala Gly Pro Met
        195                 200                 205

Gly Pro Ala Gly Glu Arg Gly Glu Lys Gly Glu Pro Gly Thr Gln Gly
    210                 215                 220

Ala Lys Gly Asp Arg Gly Glu Thr Gly Pro Val Gly Pro Arg Gly Glu
225                 230                 235                 240

Arg Gly Glu Ala Gly Pro Ala Gly Lys Asp Gly Glu Arg Gly Pro Val
                245                 250                 255

Gly Pro Ala Gly Lys Asp Gly Gln Asn Gly Gln Asp Gly Leu Pro Gly
            260                 265                 270

Lys Asp Gly Lys Asp Gly Gln Asn Gly Lys Asp Gly Leu Pro Gly Lys
        275                 280                 285

Asp Gly Lys Asp Gly Gln Asn Gly Lys Asp Gly Leu Pro Gly Lys Asp
    290                 295                 300

Gly Lys Asp Gly Gln Asp Gly Lys Asp Gly Leu Pro Gly Lys Asp Gly
305                 310                 315                 320

Lys Asp Gly Leu Pro Gly Lys Asp Gly Lys Asp Gly Gln Pro Gly Lys
                325                 330                 335

Pro Ala Pro Lys Thr Pro Glu Val Pro Gln Lys Pro Asp Thr Ala Pro
            340                 345                 350
```

<210> SEQ ID NO 12
<211> LENGTH: 246
<212> TYPE: PRT
<213> ORGANISM: Artificial Sequence
<220> FEATURE:
<223> OTHER INFORMATION: Synthetic peptide

<400> SEQUENCE: 12

```
Gly Ser Pro Gly Leu Pro Gly Pro Arg Gly Gln Asp Gly Arg Asn Gly
1               5                   10                  15

Glu Arg Gly Glu Gln Gly Pro Thr Gly Pro Thr Gly Pro Ala Gly Pro
                20                  25                  30

Arg Gly Leu Gln Gly Leu Gln Gly Phe Pro Gly Glu Arg Gly Glu Gln
            35                  40                  45

Gly Pro Thr Gly Pro Ala Gly Pro Arg Gly Leu Gln Gly Glu Arg Gly
        50                  55                  60

Glu Gln Gly Pro Thr Gly Leu Ala Gly Lys Ala Gly Glu Ala Gly Ala
65                  70                  75                  80

Lys Gly Glu Thr Gly Pro Ala Gly Pro Gln Gly Pro Arg Gly Glu Gln
                85                  90                  95

Gly Pro Gln Gly Leu Pro Gly Lys Asp Gly Glu Ala Gly Ala Gln Gly
            100                 105                 110

Pro Ala Gly Pro Met Gly Pro Ala Gly Glu Arg Gly Glu Lys Gly Glu
        115                 120                 125

Pro Gly Thr Gln Gly Ala Lys Gly Asp Arg Gly Glu Thr Gly Pro Val
    130                 135                 140
```

Gly Pro Arg Gly Glu Arg Gly Glu Ala Gly Pro Ala Gly Lys Asp Gly
145                 150                 155                 160

Glu Arg Gly Pro Val Gly Pro Ala Gly Lys Asp Gly Gln Asn Gly Gln
                165                 170                 175

Asp Gly Leu Pro Gly Lys Asp Gly Lys Asp Gly Gln Asn Gly Lys Asp
            180                 185                 190

Gly Leu Pro Gly Lys Asp Gly Lys Asp Gly Gln Asn Gly Lys Asp Gly
        195                 200                 205

Leu Pro Gly Lys Asp Gly Lys Asp Gly Gln Asp Gly Lys Asp Gly Leu
    210                 215                 220

Pro Gly Lys Asp Gly Lys Asp Gly Leu Pro Gly Lys Asp Gly Lys Asp
225                 230                 235                 240

Gly Gln Pro Gly Lys Pro
                245

<210> SEQ ID NO 13
<211> LENGTH: 349
<212> TYPE: PRT
<213> ORGANISM: Artificial Sequence
<220> FEATURE:
<223> OTHER INFORMATION: Synthetic peptide

<400> SEQUENCE: 13

Met Asn His Lys Val His His His His His Met Glu Leu Asp Glu
1               5                   10                  15

Gln Glu Glu Lys Ala Lys Val Arg Thr Glu Leu Ile Gln Glu Leu Ala
                20                  25                  30

Gln Gly Leu Gly Gly Ile Glu Lys Lys Asn Phe Pro Thr Leu Gly Asp
            35                  40                  45

Glu Asp Leu Asp His Thr Tyr Met Thr Lys Leu Leu Thr Tyr Leu Gln
        50                  55                  60

Glu Arg Glu Gln Ala Glu Asn Ser Trp Arg Lys Arg Leu Leu Lys Gly
65                  70                  75                  80

Ile Gln Asp His Ala Leu Asp Asn Leu Tyr Val Gly Leu Pro Gly Pro
                85                  90                  95

Arg Gly Gln Asp Gly Arg Asn Gly Glu Arg Gly Glu Gln Gly Pro Thr
            100                 105                 110

Gly Pro Thr Gly Pro Ala Gly Pro Arg Gly Leu Gln Gly Leu Gln Gly
        115                 120                 125

Phe Pro Gly Glu Arg Gly Glu Gln Gly Pro Thr Gly Pro Ala Gly Pro
    130                 135                 140

Arg Gly Leu Gln Gly Glu Arg Gly Gln Gly Pro Thr Gly Leu Ala
145                 150                 155                 160

Gly Lys Ala Gly Glu Ala Gly Ala Lys Gly Glu Thr Gly Pro Ala Gly
                165                 170                 175

Pro Gln Gly Pro Arg Gly Glu Gln Gly Pro Gln Gly Leu Pro Gly Lys
            180                 185                 190

Asp Gly Glu Ala Gly Ala Gln Gly Pro Ala Gly Pro Met Gly Pro Ala
        195                 200                 205

Gly Glu Arg Gly Glu Lys Gly Glu Pro Gly Thr Gln Gly Ala Lys Gly
    210                 215                 220

Asp Arg Gly Glu Thr Gly Pro Val Gly Pro Arg Gly Glu Arg Gly Glu
225                 230                 235                 240

Ala Gly Pro Ala Gly Lys Asp Gly Glu Arg Gly Pro Val Gly Pro Ala
                245                 250                 255

```
Gly Lys Asp Gly Gln Asn Gly Gln Asp Gly Leu Pro Gly Lys Asp Gly
            260                 265                 270

Lys Asp Gly Gln Asn Gly Lys Asp Gly Leu Pro Gly Lys Asp Gly Lys
        275                 280                 285

Asp Gly Gln Asn Gly Lys Asp Gly Leu Pro Gly Lys Asp Gly Lys Asp
    290                 295                 300

Gly Gln Asp Gly Lys Asp Gly Leu Pro Gly Lys Asp Gly Lys Asp Gly
305                 310                 315                 320

Leu Pro Gly Lys Asp Gly Lys Asp Gly Gln Pro Gly Lys Pro Ala Pro
                325                 330                 335

Lys Thr Pro Glu Val Pro Gln Lys Pro Asp Thr Ala Pro
            340                 345
```

<210> SEQ ID NO 14
<211> LENGTH: 243
<212> TYPE: PRT
<213> ORGANISM: Artificial Sequence
<220> FEATURE:
<223> OTHER INFORMATION: Synthetic peptide

<400> SEQUENCE: 14

```
Gly Leu Pro Gly Pro Arg Gly Gln Asp Gly Arg Asn Gly Glu Arg Gly
1               5                   10                  15

Glu Gln Gly Pro Thr Gly Pro Thr Gly Pro Ala Gly Pro Arg Gly Leu
            20                  25                  30

Gln Gly Leu Gln Gly Phe Pro Gly Glu Arg Gly Glu Gln Gly Pro Thr
        35                  40                  45

Gly Pro Ala Gly Pro Arg Gly Leu Gln Gly Glu Arg Gly Glu Gln Gly
    50                  55                  60

Pro Thr Gly Leu Ala Gly Lys Ala Gly Glu Ala Gly Ala Lys Gly Glu
65                  70                  75                  80

Thr Gly Pro Ala Gly Pro Gln Gly Pro Arg Gly Glu Gln Gly Pro Gln
            85                  90                  95

Gly Leu Pro Gly Lys Asp Gly Glu Ala Gly Ala Gln Gly Pro Ala Gly
            100                 105                 110

Pro Met Gly Pro Ala Gly Glu Arg Gly Glu Lys Gly Glu Pro Gly Thr
        115                 120                 125

Gln Gly Ala Lys Gly Asp Arg Gly Glu Thr Gly Pro Val Gly Pro Arg
    130                 135                 140

Gly Glu Arg Gly Glu Ala Gly Pro Ala Gly Lys Asp Gly Glu Arg Gly
145                 150                 155                 160

Pro Val Gly Pro Ala Gly Lys Asp Gly Gln Asn Gly Gln Asp Gly Leu
                165                 170                 175

Pro Gly Lys Asp Gly Lys Asp Gly Gln Asn Gly Lys Asp Gly Leu Pro
            180                 185                 190

Gly Lys Asp Gly Lys Asp Gly Gln Asn Gly Lys Asp Gly Leu Pro Gly
        195                 200                 205

Lys Asp Gly Lys Asp Gly Gln Asp Gly Lys Asp Gly Leu Pro Gly Lys
    210                 215                 220

Asp Gly Lys Asp Gly Leu Pro Gly Lys Asp Gly Lys Asp Gly Gln Pro
225                 230                 235                 240

Gly Lys Pro
```

<210> SEQ ID NO 15
<211> LENGTH: 339
<212> TYPE: PRT

```
<213> ORGANISM: Artificial Sequence
<220> FEATURE:
<223> OTHER INFORMATION: Synthetic peptide

<400> SEQUENCE: 15

Met Asn His Lys Val His His His His His Met Glu Leu Asp Glu
1               5                   10                  15

Gln Glu Glu Lys Ala Lys Val Arg Thr Glu Leu Ile Gln Glu Leu Ala
            20                  25                  30

Gln Gly Leu Gly Gly Ile Glu Lys Asn Phe Pro Thr Leu Gly Asp
        35                  40                  45

Glu Asp Leu Asp His Thr Tyr Met Thr Lys Leu Leu Thr Tyr Leu Gln
50                  55                  60

Glu Arg Glu Gln Ala Glu Asn Ser Trp Arg Lys Arg Leu Leu Lys Gly
65                  70                  75                  80

Ile Gln Asp His Ala Leu Asp Gly Gln Asp Gly Arg Asn Gly Glu Arg
                85                  90                  95

Gly Glu Gln Gly Pro Thr Gly Pro Thr Gly Pro Ala Gly Pro Arg Gly
            100                 105                 110

Leu Gln Gly Leu Gln Gly Leu Gln Gly Glu Arg Gly Glu Gln Gly Pro
        115                 120                 125

Thr Gly Pro Ala Gly Pro Arg Gly Leu Gln Gly Glu Arg Gly Glu Gln
130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Pro Arg Gly Glu Gln Gly Val
                165                 170                 175

Met Gly Phe Pro Gly Lys Asp Gly Glu Ala Gly Ala Gln Gly Pro Ala
            180                 185                 190

Gly Pro Met Gly Pro Ala Gly Glu Arg Gly Glu Lys Gly Glu Pro Gly
        195                 200                 205

Thr Gln Gly Ala Lys Gly Asp Arg Gly Glu Thr Gly Pro Val Gly Pro
210                 215                 220

Arg Gly Glu Arg Gly Glu Ala Gly Pro Ala Gly Lys Asp Gly Glu Arg
225                 230                 235                 240

Gly Pro Val Gly Pro Ala Gly Lys Asp Gly Gln Asn Gly Gln Asp Gly
                245                 250                 255

Leu Pro Gly Lys Asp Gly Lys Asp Gly Gln Asn Gly Lys Asp Gly Leu
            260                 265                 270

Pro Gly Lys Asp Gly Lys Asp Gly Gln Asn Gly Lys Asp Gly Leu Pro
        275                 280                 285

Gly Lys Asp Gly Lys Asp Gly Gln Asp Gly Lys Asp Gly Leu Pro Gly
    290                 295                 300

Lys Asp Gly Lys Asp Gly Leu Pro Gly Lys Asp Gly Lys Asp Gly Gln
305                 310                 315                 320

Pro Gly Lys Pro Ala Pro Lys Thr Pro Glu Val Pro Gln Lys Pro Asp
                325                 330                 335

Thr Ala Pro

<210> SEQ ID NO 16
<211> LENGTH: 237
<212> TYPE: PRT
<213> ORGANISM: Artificial Sequence
<220> FEATURE:
<223> OTHER INFORMATION: Synthetic peptide
```

<400> SEQUENCE: 16

```
Gly Gln Asp Gly Arg Asn Gly Glu Arg Gly Glu Gln Gly Pro Thr Gly
1               5                   10                  15
Pro Thr Gly Pro Ala Gly Pro Arg Gly Leu Gln Gly Leu Gln Gly Leu
            20                  25                  30
Gln Gly Glu Arg Gly Glu Gln Gly Pro Thr Gly Pro Ala Gly Pro Arg
        35                  40                  45
Gly Leu Gln Gly Glu Arg Gly Glu Gln Gly Pro Thr Gly Leu Ala Gly
    50                  55                  60
Lys Ala Gly Glu Ala Gly Ala Lys Gly Glu Thr Gly Pro Ala Gly Pro
65                  70                  75                  80
Gln Gly Pro Arg Gly Glu Gln Gly Val Met Gly Phe Pro Gly Lys Asp
                85                  90                  95
Gly Glu Ala Gly Ala Gln Gly Pro Ala Gly Pro Met Gly Pro Ala Gly
            100                 105                 110
Glu Arg Gly Glu Lys Gly Glu Pro Gly Thr Gln Gly Ala Lys Gly Asp
                115                 120                 125
Arg Gly Glu Thr Gly Pro Val Gly Pro Arg Gly Glu Arg Gly Glu Ala
        130                 135                 140
Gly Pro Ala Gly Lys Asp Gly Glu Arg Gly Pro Val Gly Pro Ala Gly
145                 150                 155                 160
Lys Asp Gly Gln Asn Gly Gln Asp Gly Leu Pro Gly Lys Asp Gly Lys
                165                 170                 175
Asp Gly Gln Asn Gly Lys Asp Gly Leu Pro Gly Lys Asp Gly Lys Asp
            180                 185                 190
Gly Gln Asn Gly Lys Asp Gly Leu Pro Gly Lys Asp Gly Lys Asp Gly
        195                 200                 205
Gln Asp Gly Lys Asp Gly Leu Pro Gly Lys Asp Gly Lys Asp Gly Leu
    210                 215                 220
Pro Gly Lys Asp Gly Lys Asp Gly Gln Pro Gly Lys Pro
225                 230                 235
```

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 17

```
Gly Xaa Tyr Gly Xaa Tyr Gly Xaa Tyr Gly Xaa Tyr
1               5                   10
```

<210> SEQ ID NO 18
<211> LENGTH: 6

```
<212> TYPE: PRT
<213> ORGANISM: Artificial Sequence
<220> FEATURE:
<223> OTHER INFORMATION: Synthetic peptide

<400> SEQUENCE: 18

Gly Leu Pro Gly Glu Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Gly Leu Pro Gly Glu Asn
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Gly Leu Pro Gly Glu Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Gly Arg Pro Gly Glu Arg
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Gly Arg Pro Gly Glu Asn
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Gly Arg Pro Gly Glu Lys
1               5

<210> SEQ ID NO 24
<211> LENGTH: 6
<212> TYPE: PRT
```

```
<213> ORGANISM: Artificial Sequence
<220> FEATURE:
<223> OTHER INFORMATION: Synthetic peptide

<400> SEQUENCE: 24

Gly Phe Pro Gly Glu Arg
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Gly Phe Pro Gly Glu Asn
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Gly Phe Pro Gly Glu Lys
1               5
```